US012376752B2

(12) United States Patent
Lee et al.

(10) Patent No.: US 12,376,752 B2
(45) Date of Patent: Aug. 5, 2025

(54) APPARATUS FOR MEASURING BIO-INFORMATION, AND ELECTRONIC DEVICE INCLUDING THE SAME

(71) Applicant: SAMSUNG ELECTRONICS CO., LTD., Suwon-si (KR)

(72) Inventors: Tak Hyung Lee, Seoul (KR); Byung Hoon Ko, Hwaseong-si (KR); Jong Wook Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 328 days.

(21) Appl. No.: 17/208,287

(22) Filed: Mar. 22, 2021

(65) Prior Publication Data

US 2022/0087549 A1 Mar. 24, 2022

(30) Foreign Application Priority Data

Sep. 22, 2020 (KR) .................. 10-2020-0122111

(51) Int. Cl.
*A61B 5/021* (2006.01)
*A61B 5/00* (2006.01)

(52) U.S. Cl.
CPC .......... *A61B 5/02108* (2013.01); *A61B 5/681* (2013.01)

(58) Field of Classification Search
CPC ... A61B 5/02108; A61B 5/681; A61B 5/0261; A61B 5/1455; A61B 5/02141;
(Continued)

(56) References Cited

U.S. PATENT DOCUMENTS 8,231,522 B2 7/2012 Endo et al.
9,307,600 B2 4/2016 Upton
(Continued)

FOREIGN PATENT DOCUMENTS

EP 3499867 A1 6/2019
JP 2010-68992 A 4/2010
(Continued)

OTHER PUBLICATIONS

US 10,830,577 B2, 11/2020, Wang et al. (withdrawn)
Communication issued Jan. 5, 2022 by the European Patent Office in European Patent Application No. 21186719.7.

*Primary Examiner* — Tse W Chen
*Assistant Examiner* — Joseph A Tombers
(74) *Attorney, Agent, or Firm* — Sughrue Mion, PLLC

(57) ABSTRACT

An apparatus for measuring bio-information includes: a light source including a first light emitter that emits first light of a first wavelength, and a second light emitter that emits second light of a second wavelength; an image sensor including a first pixel region including first pixels that detect the first light reacted with an object, and a second pixel region including second pixels that detect the second light reacted with the object; a light source controller that controls the first light emitter to emit the first light of the first wavelength when a first light exposure operation is performed on the first pixels, and controls the second light emitter to emit the second light of the second wavelength when a second light exposure operation is performed on the second pixels; and a processor that obtains a bio-signal of the object from data detected by the image sensor.

12 Claims, 29 Drawing Sheets

(58) Field of Classification Search
CPC . A61B 5/02007; A61B 5/024; A61B 5/14532; A61B 5/14551; A61B 5/6803; A61B 5/0059; A61B 5/6843; A61B 5/6898; A61B 2562/0233; H04N 23/74; H04N 25/531; H04N 23/73
See application file for complete search history.

(56) References Cited

U.S. PATENT DOCUMENTS

| | | | |
|---|---|---|---|
| 9,593,982 | B2 | 3/2017 | Rhoads et al. |
| 9,661,308 | B1 | 5/2017 | Wang et al. |
| 10,132,616 | B2 | 11/2018 | Wang |
| 10,145,678 | B2 | 12/2018 | Wang et al. |
| 10,250,833 | B2 | 4/2019 | Wang et al. |
| 10,356,380 | B2 | 7/2019 | You et al. |
| 10,447,958 | B2 | 10/2019 | Wang et al. |
| 10,575,720 | B2 | 3/2020 | Kagawa |
| 10,704,896 | B2 | 7/2020 | Wang |
| 10,718,605 | B2 | 7/2020 | Wang |
| 10,764,505 | B2 | 9/2020 | Takemoto et al. |
| 10,883,821 | B2 | 1/2021 | Wang |
| 10,883,822 | B2 | 1/2021 | Wang |
| 10,893,227 | B2 | 1/2021 | Wang et al. |
| 2008/0266425 | A1* | 10/2008 | Shurboff ............... H04N 25/60 348/E5.037 |
| 2014/0288390 | A1 | 9/2014 | Hong et al. |
| 2015/0163421 | A1 | 6/2015 | Shigeta |
| 2015/0271886 | A1 | 9/2015 | Upton |
| 2016/0173801 | A1 | 6/2016 | Wang et al. |
| 2016/0309135 | A1 | 10/2016 | Ovsiannikov et al. |
| 2016/0310027 | A1* | 10/2016 | Han ..................... A61B 5/6898 |
| 2017/0014059 | A1 | 1/2017 | Koshiba |
| 2017/0079591 | A1* | 3/2017 | Gruhlke ............... A61B 5/7278 |
| 2017/0238791 | A1 | 8/2017 | Kagawa |
| 2017/0337412 | A1 | 11/2017 | Bhat et al. |
| 2018/0288388 | A1* | 10/2018 | Hicks ................... H01S 5/0071 |
| 2018/0349697 | A1* | 12/2018 | Kang .................. H04N 25/745 |
| 2019/0052863 | A1 | 2/2019 | Yang |
| 2019/0216340 | A1* | 7/2019 | Holz .................... A61B 5/6844 |
| 2020/0370881 | A1 | 11/2020 | Wang et al. |
| 2021/0041225 | A1 | 2/2021 | Wang |
| 2021/0041226 | A1 | 2/2021 | Wang |

FOREIGN PATENT DOCUMENTS

| | | |
|---|---|---|
| JP | 6072372 B2 | 2/2017 |
| KR | 10-2016-0124664 A | 10/2016 |
| KR | 10-2017-0050058 A | 5/2017 |
| KR | 10-2019-0007634 A | 1/2019 |
| KR | 10-2019-0105281 A | 9/2019 |
| KR | 10-2029003 B1 | 10/2019 |

* cited by examiner

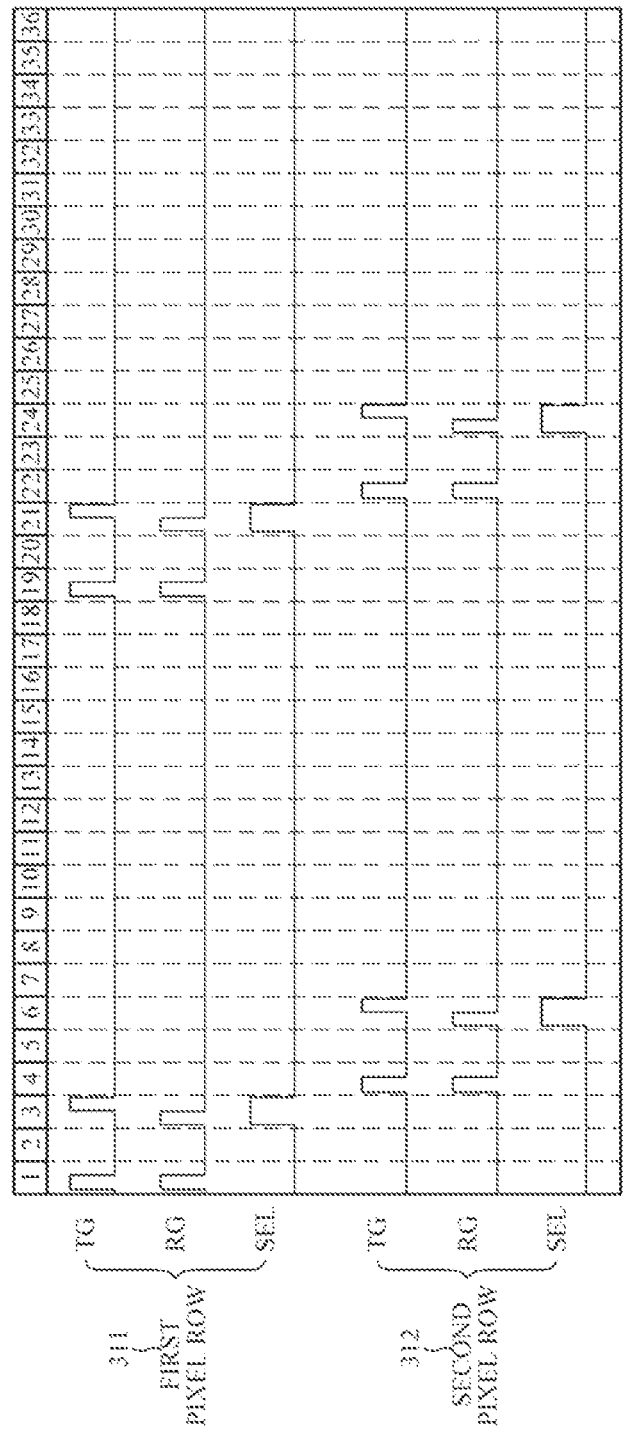

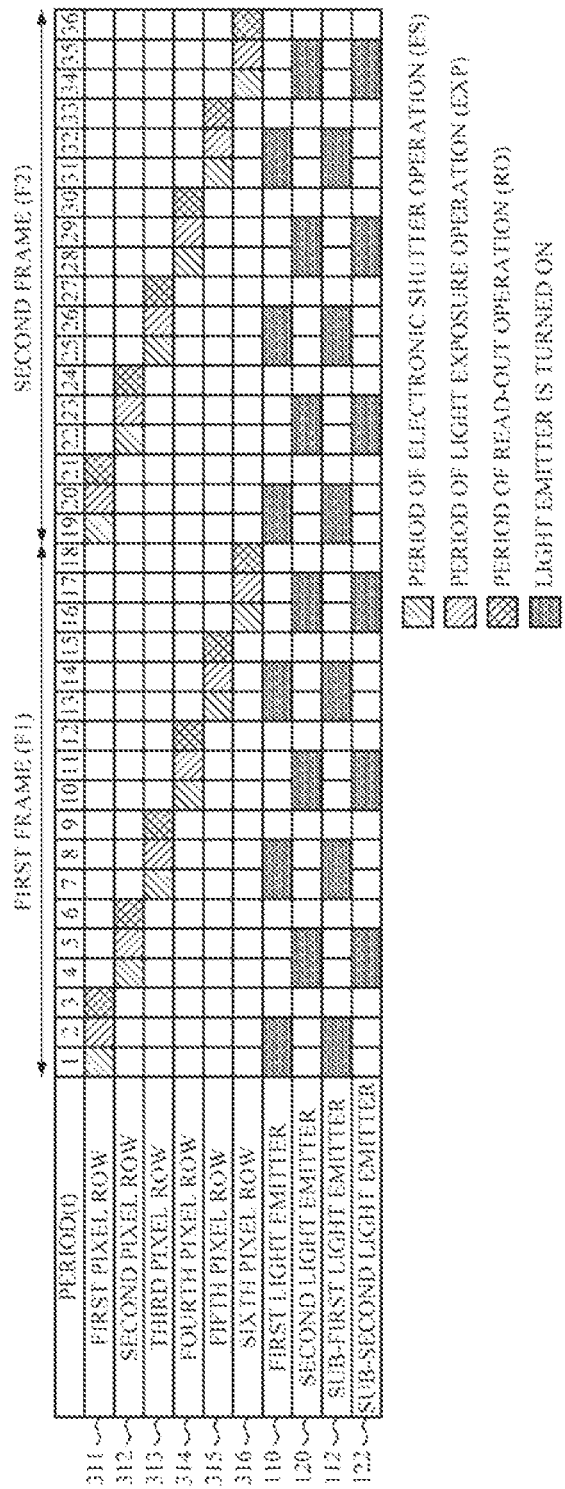

APPARATUS FOR MEASURING BIO-INFORMATION, AND ELECTRONIC DEVICE INCLUDING THE SAME

CROSS-REFERENCE TO RELATED APPLICATION(S)

This application claims priority from Korean Patent Application No. 10-2020-0122111, filed on Sep. 22, 2020, in the Korean Intellectual Property Office, the disclosure of which is incorporated by reference herein in its entirety.

BACKGROUND

1. Field

Apparatuses and methods consistent with example embodiments relate to measuring bio-information, such as blood pressure, by using a light source and an image sensor.

2. Description of the Related Art

As interest in medical devices is growing with the development of medical science and the extended average life span, not only large medical devices for use in hospitals or medical examination institutions, but also small medical devices that individuals can carry are being developed. Medical devices for measuring bio-information are generally divided into invasive type devices and non-invasive type devices. The non-invasive type device has an advantage of detecting bio-information without causing pain to a subject, but has a drawback in that accuracy of the measurement result is low. Accordingly, various studies are conducted to overcome such drawback.

SUMMARY

Example embodiments address at least the above problems and/or disadvantages and other disadvantages not described above. Also, the example embodiments are not required to overcome the disadvantages described above, and may not overcome any of the problems described above.

According to an aspect of an example embodiment, there is provided an apparatus for measuring bio-information, the apparatus including: a light source including a first light emitter configured to emit first light of a first wavelength, and a second light emitter configured to emit a second light of second wavelength; an image sensor including: a first pixel region including a plurality of first pixels configured to detect the first light emitted by the first light emitter and reacted with an object, and a second pixel region including a plurality of second pixels configured to detect the second light emitted by the second light emitter and reacted with the object; a light source controller configured to control the first light emitter to emit the first light of the first wavelength when a first light exposure operation is performed on the plurality of first pixels, and control the second light emitter to emit the second light of the second wavelength when a second light exposure operation is performed on the plurality of second pixels; and a processor configured to obtain a bio-signal of the object from data that is detected by the image sensor while the light source is operated by the light source controller, wherein the image sensor comprises ten or more pixel rows, and wherein a first pixel row included in the first pixel region is different from a second pixel row included in the second pixel region.

The first pixel region may include the ten or more pixel rows.

The image sensor may include a pixel controller configured to generate pixel control signals and timing signals for controlling the plurality of first pixels and the plurality of second pixels, and the light source controller may be further configured to control the light source based on the pixel control signals or the timing signals.

The pixel control signals may include a reset signal, and the timing signals comprise a horizontal synchronization signal, and the light source controller may be further configured to control the light source based on the reset signal or the horizontal synchronization signal.

The image sensor may be operated at a sampling rate in a range of 15 Hz to 1000 Hz.

The light source may include a third light emitter configured to emit a third light of a third wavelength.

The light source may include: a sub-first light emitter configured to emit a fourth light of the first wavelength; and a sub-second light emitter configured to emit a fifth light of the second wavelength.

The apparatus may include a force sensor disposed on the image sensor to measure a force exerted onto the apparatus.

The bio-information may include blood pressure.

The image sensor may include: a third pixel region including a plurality of third pixels configured to detect the first light emitted by the first light emitter and reacted with the object; and a fourth pixel region including a plurality of fourth pixels configured to detect the second light emitted by the second light emitter and reacted with the object.

The plurality of first pixels in the first pixel region, the plurality of second pixels in the second pixel region, the plurality of third pixels in the third region, and the plurality of fourth pixels in the fourth pixel region may be arranged in different pixel rows from each other.

According to an aspect of an example embodiment, there is provided a method of measuring bio-information, including: based on a pixel control signal or a timing signal which is generated by an image sensor, driving a first light emitter to emit first light of a first wavelength; detecting the first light of the first wavelength, which is reacted with an object, by using a plurality of first pixels included in a first pixel region of the image sensor; based on the pixel control signal or the timing signal which is generated by the image sensor, driving a second light emitter to emit second light of a second wavelength; detecting the second light of the second wavelength, which is reacted with the object, by using a plurality of second pixels included in a second pixel region of the image sensor; and measuring the bio-information based on data obtained from the first and second pixel regions of the image sensor.

The image sensor may include ten or more pixel rows, and a first pixel row included in the first pixel region may be different from a second pixel row included in the second pixel region.

A first period of time during which a first light exposure operation is performed on the first pixel region may not overlap a second period of time during which a second light exposure operation is performed on the second pixel region.

The method may include measuring a force exerted by the object onto an apparatus including the first and the second emitters and the image sensor.

The method may include: detecting the first light, which is emitted by the first light emitter and reacted with the object, by using a plurality of third pixels included in a third pixel region of the image sensor; and detecting the second light, emitted by the second light emitter and reacted with the object, by using a plurality of fourth pixels included in a fourth pixel region of the image sensor.

The plurality of first pixels in the first pixel region, the plurality of second pixels in the second pixel region, the plurality of third pixels in the third region, and the plurality of fourth pixels in the fourth pixel region may be arranged in different pixel rows from each other.

The bio-information may include blood pressure.

The timing signal may be a horizontal synchronization signal, and the driving the first light emitter and the driving the second light emitter may include driving the first light emitter based on the horizontal synchronization signal, and driving the second light emitter based on the horizontal synchronization signal, respectively.

The pixel control signal may be a pixel reset signal, and the driving the first light emitter and the driving the second light emitter may include driving the first light emitter based on the pixel reset signal, and driving the second light emitter based on the pixel reset signal, respectively.

According to an aspect of an example embodiment, there is provided an electronic device including an apparatus for measuring bio-information, a processor configured to control an operation of the apparatus, and a sound output device or a display device configured to output information measured by the apparatus. The apparatus may include: a light source including a first light emitter configured to emit first light of a first wavelength, and a second light emitter configured to emit second light of a second wavelength; an image sensor including a first pixel region including a plurality of first pixels configured to detect the first light that is emitted by the first light emitter and reacted with an object, and a second pixel region including a plurality of second pixels configured to detect the second light that is emitted by the second light emitter and reacted with the object; a light source controller configured to control the first light emitter to emit the first light of the first wavelength when a first light exposure operation is performed on the plurality of first pixels, and control the second light emitter to emit the second light of the second wavelength when a second light exposure operation is performed on the plurality of second pixels. The processor is configured to obtain a bio-signal of the object from data that is detected by the image sensor while the light source is operated by the light source controller. The image sensor may include ten or more pixel rows. A first pixel row included in the first pixel region may be different from a second pixel row included in the second pixel region.

The first pixel region may include the ten or more pixel rows.

The image sensor may include a pixel controller configured to generate pixel control signals and timing signals for controlling the plurality of first pixels and the plurality of second pixels, and the light source controller may be further configured to control the light source based on the pixel control signals or the timing signals.

The pixel control signals may include a reset signal, and the timing signals may include a horizontal synchronization signal. The light source controller may be further configured to control the light source based on the reset signal, or the horizontal synchronization signal.

The image sensor may be operated at a sampling rate in a range of 15 Hz to 1000 Hz.

The light source may include a third light emitter configured to emit a third light of a third wavelength.

The light source may include: a sub-first light emitter configured to emit a fourth light of the first wavelength; and a sub-second light emitter configured to emit a fifth light of the second wavelength.

The electronic device may include a force sensor disposed on the image sensor to measure a force exerted onto the apparatus or the electronic device.

The bio-information may include blood pressure.

The image sensor may include: a third pixel region including a plurality of third pixels configured to detect the first light emitted by the first light emitter and reacted with the object; and a fourth pixel region including a plurality of fourth pixels configured to detect the second light emitted by the second light emitter and reacted with the object.

The plurality of first pixels in the first pixel region, the plurality of second pixels in the second pixel region, the plurality of third pixels in the third region, and the plurality of fourth pixels in the fourth pixel region may be arranged in different pixel rows from each other.

According to an aspect of another example embodiment, there is provided an apparatus for measuring bio-information, the apparatus including: a light source configured to emit first light of a first wavelength and second light of a second wavelength to an object; an image sensor including: a first pixel line comprising a plurality of first pixels which are exposed to the first light together at a first period of time; and a second pixel line comprising a plurality of second pixels which are exposed to the second light together at a second period time; a light source controller configured to control the light source to emit the first light during the first period of time, and control the light source to emit the second light during the second period time; and a processor configured to obtain the bio-information based on data collected from the first pixel line and the second pixel line of the image sensor.

The image sensor may be configured to generate and provide a reset signal to the light source controller, and the light source controller may be further configured to control a light emission time of the first light and the second light based on the reset signal.

The image sensor may be configured to generate and provide a horizontal synchronization signal to the light source controller, and the light source controller may be further configured to control a light emission time of the first light and the second light based on the horizontal synchronization signal.

BRIEF DESCRIPTION OF THE DRAWINGS

The above and/or other aspects will be more apparent by describing certain example embodiments, with reference to the accompanying drawings, in which:

FIG. 4 is a diagram explaining a pixel control signal provided to first and second pixel rows of FIG. 3;

FIG. 13A is a diagram explaining an example of a method of driving a light source of FIG. 12;

DETAILED DESCRIPTION

Figure 1:
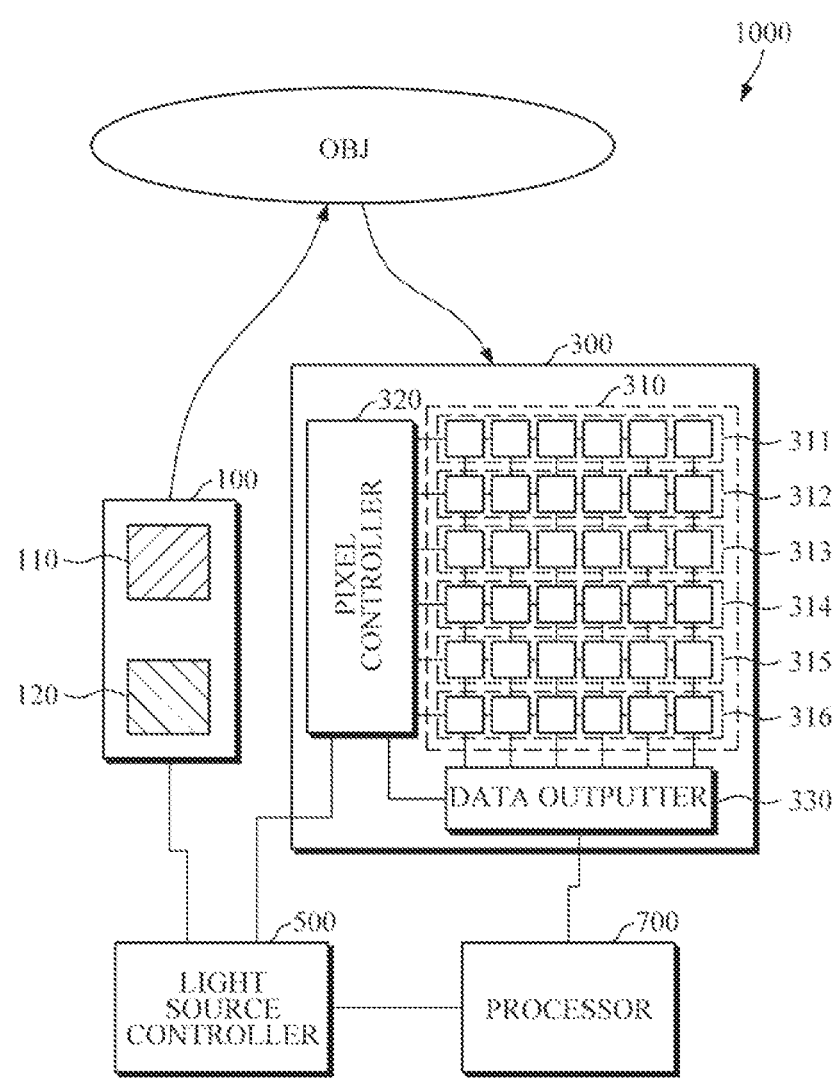
FIG. 1 is a schematic diagram illustrating a configuration of an apparatus for measuring bio-information according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

In the present disclosure, the expression "A or B," or A and/or B" may include all possible combinations of listed items. It will be understood that, although the terms "first," "second," may be used herein to describe various elements without regarding to sequence and/or importance, these elements should not be limited by these terms. These terms are only used to distinguish one element from another.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

In the following description of embodiments, when a certain element is coupled with/to or connected to another element, it should be understood that the certain element may be connected to another element directly or via another element in the middle. In contrast, when a certain element is directly connected or directly linked to another element, it should be understood that any other element does not exist in the middle. In addition, unless explicitly described to the contrary, an expression such as "comprising" or "including" will be understood to imply the inclusion of stated elements but not the exclusion of any other elements. However, the term "including" should not be construed as including all the components or steps stated in the present disclosure.

Embodiments of the present disclosure, which will be described below, relate to technology in the field of the apparatus for measuring bio-information (e.g., apparatus for measuring blood pressure). Hereinafter, detailed descriptions of technical features that are widely known to one of ordinary skill in the art will be omitted.

Figure 2A:
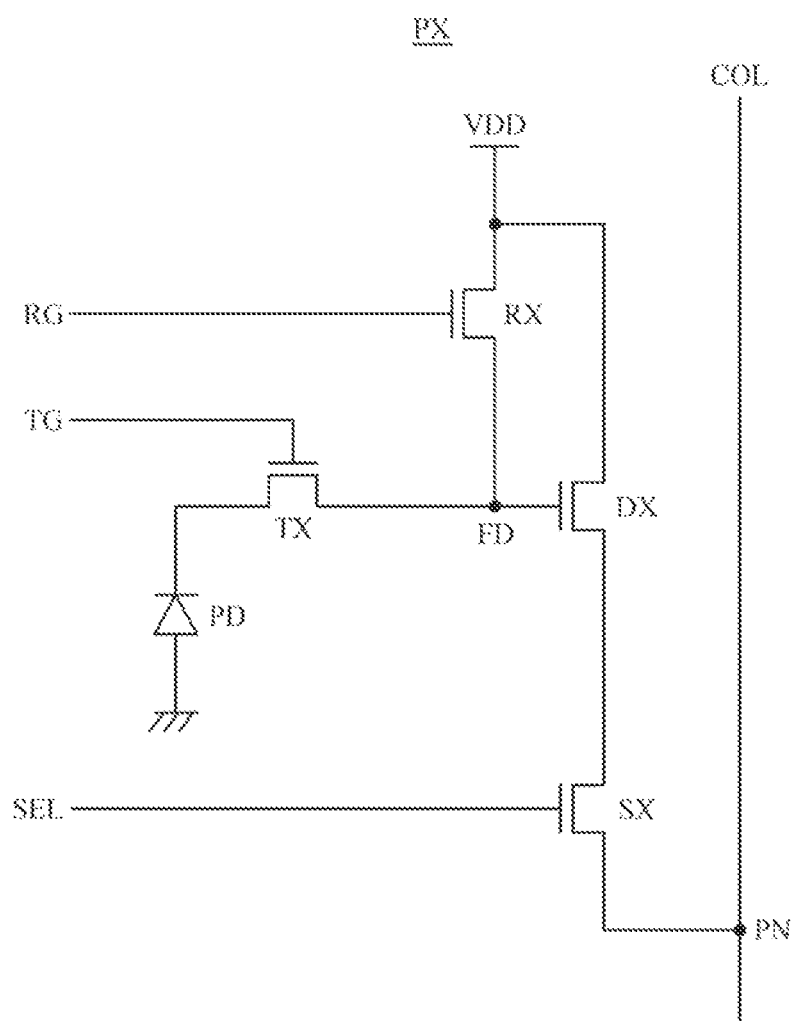
FIG. 2A is a diagram illustrating a structure of a unit pixel included in a pixel part of FIG. 1.

FIG. 1 is a schematic diagram illustrating a configuration of an apparatus for measuring bio-information according to an example embodiment of the present disclosure, and FIG. 2A is a diagram illustrating a structure of a unit pixel included in a pixel part of FIG. 1.

Bio-information may be biological/medical information which may be obtained from an object OBJ to be measured, and examples thereof may include blood pressure, blood glucose, body fat, heart rate, blood oxygen saturation level, vascular compliance, blood flow rate, or arterial stiffness. The object OBJ may be a body part at which bio-information may be easily measured, and may be, for example, an area on the inside of the wrist that is adjacent to the radial artery, an upper portion of the wrist where veins or capillaries are located, or a peripheral part of the body, such as fingers, toes, etc., where blood vessels are densely located.

Referring to FIG. 1, an apparatus 1000 for measuring bio-information includes a light source 100 for emitting light onto the object OBJ, an image sensor 300 for detecting reacted light, such as light scattered or reflected from or transmitted through the object OBJ, a light source controller 500 for controlling the light source 100, and a processor 700 for measuring bio-information from a signal detected by the image sensor 300.

The light source 100 may emit two or more light beams to the object OBJ. The two or more light beams may have different wavelengths and may reach different depths of the object OBJ. Referring to FIG. 1, the light source 100 may include a first light emitter 110 for emitting light of a first wavelength, and a second light emitter 120 for emitting light of a second wavelength. The light of the first wavelength may be light of a short wavelength and may reach a shallower depth of the object OBJ than the light of the second wavelength. For example, the light of the first wavelength may be a green light in a wavelength range from 500 nm to 565 nm, and may be capable of penetrating into capillary vessels. The light of the second wavelength may be light of a long wavelength and may reach a greater depth of the object OJB. For example, the light of the second wavelength may be an infrared light in a wavelength range from 750 nm to 2500 nm, and may be capable of penetrating into the arteriole. The first and second light emitters 110 and 120 may be a light emitting diode (LED), a laser diode (LD), a phosphor, and/or a combination thereof. For example, both the first and second light emitters 110 and 120 may be LED light sources, or the first light emitter 110 may be an LED light source and the second light emitter 120 may be an LD light source.

The image sensor 300 is an electronic device for detecting light reacted with the object OBJ and generating an electric signal, and may include a pixel part 310, a pixel controller 320, and a data outputter 330. The image sensor 330 may be a Complementary Metal Oxide Semiconductor (CMOS) image sensor.

The pixel part 310 may accumulate an electric charge by reacting to light, reflected from the object OBJ, according to a driving signal provided from the pixel controller 320, may generate a pixel signal by detecting a potential change caused by the accumulated electric charge, and may transmit the generated pixel signal to the data outputter 330. The pixel part 310 may include pixels arranged in the form of a matrix, for example, pixels arranged in a 6×6 matrix, as illustrated in FIG. 1. Pixels arranged in the same row may be referred to as a pixel row, and the pixel part 310 may include one to six pixel rows 311 to 316. Although FIG. 1 illustrates six (6) pixel rows due to the limited space in the drawings, the image sensor 300 may include ten or more pixel rows so that the light source 100 may be controlled at a speed lower than the speed of controlling a single pixel row. A unit pixel may include a photoelectric conversion device, and a plurality of transistors for processing photo-charge output from the photoelectric conversion device, an example of which is illustrated in FIG. 2. The photoelectric conversion device may be a photo diode, a photo transistor, a photogate, a pinned photo diode, and the like. The pixel part 310 may include 100 to 5000 pixel rows, and 80 to 2000 pixel columns.

The pixel part 310 may include super pixels having a horizontal side and/or a vertical side, the length of which is twice as large as the other pixels such that the super pixels are disposed over two columns and/or two rows. Further, the pixel part 30 may include an optical filter, formed in a partial or entire region, for passing light in only a specific wavelength range.

FIG. 2A illustrates an example in which the unit pixel included in the pixel part of FIG. 1 pixel has a four-transistor (4T) structure.

Referring to FIG. 2A, each unit pixel PX may include a photo diode PD and a pixel circuit. The pixel circuit may include a floating diffusion FD, a transfer transistor TX, a reset transistor RX, a drive transistor DX, and a selection transistor SX.

The floating diffusion FD is a triple junction of the transfer transistor TX, the reset transistor RX, and the drive transistor DX, and may be a portion in which an electric charge, photoelectrically converted by the photo diode PD, is accumulated to be converted into a voltage. The transfer transistor TX is turned on to transfer the electric charge, photoelectrically converted by the photo diode PD, to the floating diffusion FD. The reset transistor RX is turned on to convert a voltage of the floating diffusion FD into a power supply voltage (VDD), and to remove the electric charge accumulated in the floating diffusion FC. The drive transistor DX may amplify a voltage, i.e., a signal of the electric charge accumulated in the floating diffusion FD. The select transistor SX is turned on to output a pixel signal, i.e., the voltage amplified by the drive transistor DX, to a column line COL. Among signals for controlling ON/OFF of the transistors TX, RX, and SX, a signal for controlling the transfer transistor TX is referred to as a transfer signal TG, a signal for controlling the reset transistor RX is referred to as a reset signal RG, and a signal for controlling the selection transistor SX is referred to as a selection signal SEL.

Referring back to FIG. 1, the pixel controller 320 may generate pixel control signals (TG, SG, and SEL) or timing signals for use in the image sensor 300 based on a master clock signal, that is provided from the light source controller 500 or the processor 700 (e.g., central processing unit (CPU) and the like), and/or a clock signal generated by a separate clock generator. When the master clock signal is generated from the light source controller 500 or the processor 700, the light source controller 500 or the processor 700 may include a clock circuit or clock generator (e.g., an electronic oscillator). The pixel controller 320 may provide the generated pixel control signals to the outside of the image sensor 300.

The timing signal, generated by the pixel controller 320, may be a pixel clock serving as a reference for a series of operations performed by the image sensor 300, including a photoelectric conversion operation of the pixel part 310, an analog digital conversion operation of the data outputter 330, and the like. Alternatively, the timing signal may be a reference signal for differentiating pixel signals, output from the image sensor 300, in units of rows or frames, and may be, for example, a horizontal synchronization signal H-sync which indicates completion of sampling of a pixel signal read-out from a pixel row, or a vertical synchronization signal V-sync which indicates completion of sampling of a pixel signal of a frame. A plurality of pixels in the same pixel row may be exposed to light at the same time, and the term "pixel row" may be also referred to as a "pixel line."

The pixel control signals, generated by the pixel controller 320, may be the transfer signal TG, the reset signal RG, and the selection signal SEL as described above, and the pixel controller 320 may drive the pixel part 310 by a rolling shutter method in which the pixel rows are sequentially exposed to light and are read out. For example, a rolling shutter may expose a frame line after line (e.g., a row after row), and the number of exposures to light may equal the number of lines (e.g., the number of rows) in the frame.

The pixel controller 320 may transmit the timing signals and/or the pixel control signals TG, RG, and SEL to an external device (e.g., the light source, 100, the light source controller 500 and/or a display device), through an interface of the image sensor 300, so that the external device interworks with the image sensor 300.

Figure 2B:
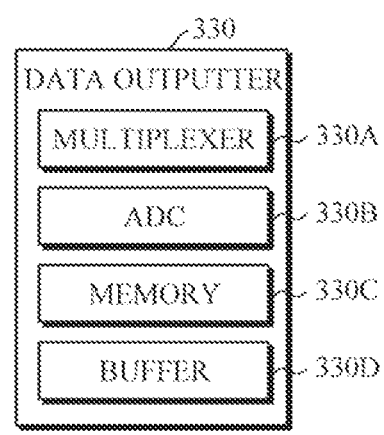
FIG. 2B illustrates a structure of a data outputter according to an example embodiment.

As shown in FIG. 2B, the data outputter 330 may include a multiplexer 330A and an analog-to-digital converter (ADC) 330B. The multiplexer 330A may receive pixel signals in an analog form from the pixel part 310 and may combine the received pixel signals into one or more analog signals. The ADC 330B may convert the one or more analog signals into a digital signal. Specifically, the ADC 330B may compare an amplitude of an analog pixel signal, on which correlated double sampling is performed, with that of a ramp signal to generate a comparison signal corresponding to a difference in amplitude between the correlated double sampled signal and the ramp signal, and may convert the pixel signal into a digital signal by counting the comparison signal. The data outputter 330 may include a memory 330C for storing digital signals and an amplifier 330D for sensing and amplifying the digital signals.

Referring back to FIG. 1, the light source controller 500 may receive the timing signals or the pixel control signals TG, RG, and SEL which are generated by the pixel controller 320, and may synchronize the operation of the light source 100 with the image sensor 300. For example, the light source controller 500 may control the light source 100 in such a manner that during a light exposure operation EXP of the first pixel row 311, the light source controller 500 may turn on the first light emitter 110 and turn off the second light emitter 120 so that the pixels included in the first pixel row 311 may detect light of the first wavelength; and during a light exposure operation EXP of the second pixel row 312, the light source controller 500 may turn off the first light emitter 110 and turn on the second light emitter 120 so that the pixels included in the second pixel row 312 may detect light of the second wavelength.

In an example embodiment, the light source controller 500 may include one or more switching elements 500A and 500B to turn on and off the first light emitter 110 and the second light emitter 120. Examples of the switching elements 500A and 500B include a relay, a Bipolar Junction Transistor (BJT), a Field Effect Transistor (FET), and a Metal Oxide Semiconductor Field Effect Transistor (MOSFET).

Figure 2C:
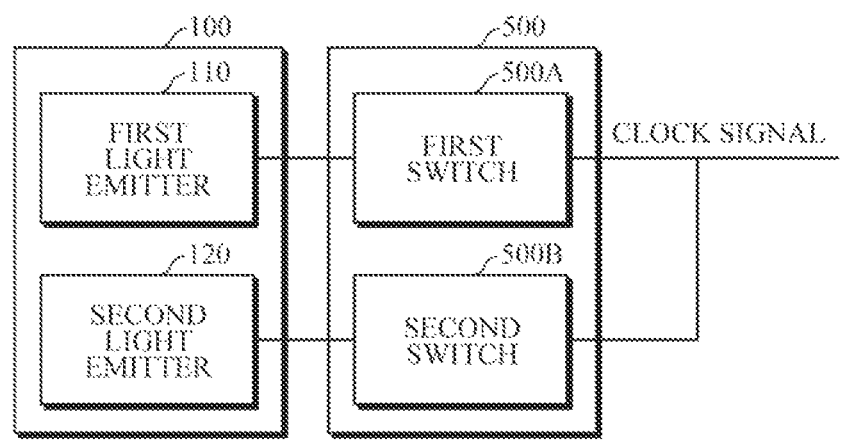
FIGS. 2C and 2D illustrate a structure of a light source controller 500 according to an example embodiment.

As shown in FIG. 2C, the light source controller 500 may turn on a first switch 500A connected to the first light emitter 110, and turn off a second switch connected to the second light emitter 120, during the light exposure operation EXP of the first pixel row 311. The light source controller 500 may turn off the first switch 500A connected to the first light emitter 110, and turn on the second switch connected to the second light emitter 120, during the light exposure operation EXP of the second pixel row 312.

Figure 2D:
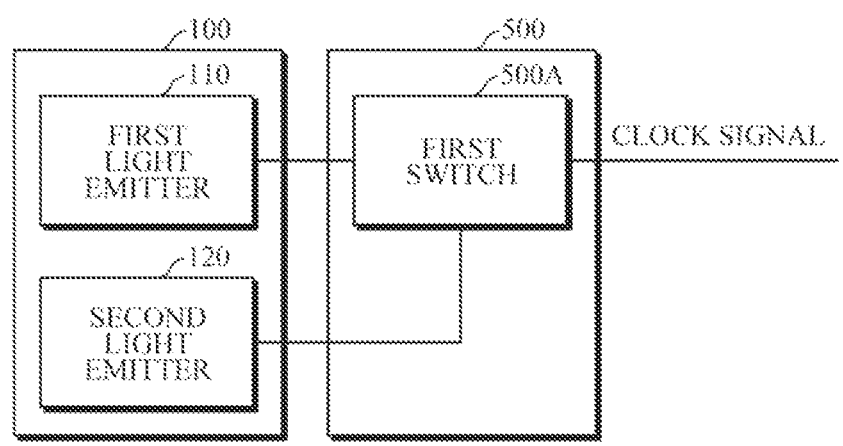

As shown in FIG. 2D, the light source controller 500 may control the first switch 500A to be connected to the first light emitter 110 and disconnected from the second light emitter 120, during the light exposure operation EXP of the first pixel row 311. On the other hand, the light source controller 500 may control the first switch 500A to be disconnected from the first light emitter 110 and connected to the second light emitter 120, during the light exposure operation EXP of the second pixel row 312.

The processor 700 may measure bio-information by using data output by the image sensor 300. The output data of the image sensor 300, which is received by the processor 700, includes data on the light intensity detected by the pixels of the pixel part 310, and the processor 700 may analyze or extract bio-information by analyzing the received data. The operation of the processor 700 will be described below with reference to FIG. 3.

Hereinafter, an example of a method of measuring blood pressure as bio-information by using the apparatus 1000 for measuring bio-information of FIG. 1 will be described with reference to FIGS. 3 and 4.

Figure 3:
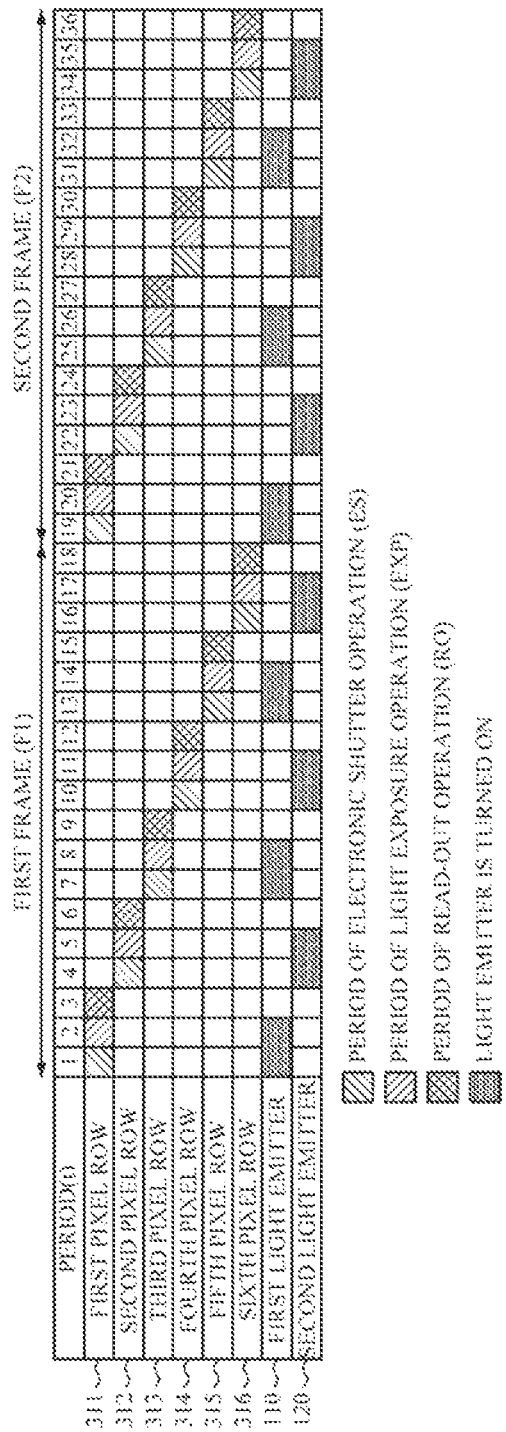
FIG. 3 is a diagram explaining an operation of a pixel part and a light source of FIG. 1.

FIG. 3 is a diagram explaining an operation timing of pixel rows and light emitters of FIG. 1, and FIG. 4 is a diagram explaining a timing for providing pixel control signals applied to first and second pixel rows of FIG. 3.

Referring to FIG. 3, pixel rows 311 to 316 may sequentially perform an electronic shutter operation ES, a light exposure operation EXP, and a read-out operation RO according to the pixel control signals TX, RX, and SEL of the pixel controller 320. For example, the first pixel row 311 may perform the electronic shutter operation ES in a first period t1, the light exposure operation EXP in a second period t2, and the read-out operation RO in a third period t3; subsequently, the second pixel row 312 may perform the electronic shutter operation ES, the light exposure operation EXP, and the read-out operation RO in fourth to sixth periods t4 to t6. In FIG. 3, a horizontal axis represents a sequence of operations performed by the pixel part 310, and the number of periods or intervals between the periods do not indicate the length of time. For example, the second period t2 may be longer in time than the first period t1 and the third period t3.

More specifically with reference to FIG. 4, in order to reset the first pixel row 311, the pixel controller 320 may first transmit the reset signal RG and the transfer signal TG at the same time to the pixels included in the first pixel row 311 in the first period t1, and may remove the electric charge remaining in the photo diode PD and the floating diffusion FD of the pixel PX. The operation of removing the electric charge remaining in the photo diode PD and the floating diffusion FD may be referred to as the electronic shutter operation ES. The pixel controller 320 may also transmit the reset signal RG, not only to the first pixel row 311 but also to the light source controller 500, and the light source controller 500 may turn on the first light emitter 110. In the second period t2 of FIG. 3, among photons emitted by the first light emitter 110, photons reacted with the object OBJ may be incident on the photo diode PD to be photoelectrically converted. As described above, after the electronic shutter operation ES, the operation of accumulating the electric charge by the incident photons may be referred to as the light exposure operation EXP. When the first light emitter 110 is turned on/off in response to a rising edge of the reset signal RG, the electric charge is not accumulated if the reset signal RG is in a high state, such that a period of an actual light exposure operation EXP, which lasts from a falling edge of the reset signal RG in the first period t1 to the rising edge of the reset signal RG in the third period t3, is longer than the second period t2. However, a general period of the light exposure operation EXP is sufficiently longer than the first period t1 or the third period t3, such that for convenience of explanation, the second period t2 may be referred to as the period of the light exposure operation EXP.

Then, in the third period t3, the pixel controller 320 may transmit the reset signal RG and the selection signal SEL to the first pixel row 311 to sample a reset voltage, and may transmit the transfer signal TG at a time when the reset signal RG ends, so as to sample a light exposure voltage generated by the electric charge accumulated in the photo diode PD. The reason for first sampling the reset voltage is that the respective pixels may have different voltages in a reset state, such that in order to accurately measure only the signals generated by the incident photons in the period of the light exposure operation EXP, both the reset voltage and the light exposure voltage are sampled, and then a difference between the two voltages may be used as a signal for the light exposure operation EXP. As shown in the third period t3, the operation of reading out the signal, generated by the electric charge accumulated in the light-exposed photo diode PD, and transmitting the signal to the data outputter 330, may be referred to as the read-out operation RO. In this case, the first light emitter 110 may be turned off at the rising edge of the reset signal RG transmitted in the third period t3. Subsequently, the electronic shutter operation ES of the second pixel row 312 may be performed in the fourth period t4, and the second light emitter 120 may be turned on by the reset signal RG of the fourth period t4. In the fifth period t5, photons reacted with the object OBJ, among the photons emitted by the second light emitter 120, are incident on the second pixel row 312 to be photoelectrically converted. In the sixth period t6, the read-out operation RO of the second pixel row 312 is performed, and the second light emitter 120 may be turned off at the rising edge of the reset signal RG for the second pixel row 312.

While FIG. 4 illustrates only the control signals of the first and second pixel rows 311 and 312, the electronic shutter operation ES, the light exposure operation EXP, and the read-out operation RO of the third to sixth pixel rows 313, 314, 315, and 316 may also be performed similarly in the order shown in FIG. 3. As illustrated in the timing diagram of FIG. 3, once the read-out operation RO is complete up to the sixth pixel row 316 as a last pixel row, it is considered that the pixel signal for the first frame F1 is transmitted to the data outputter 330. Once the first frame F1 is finished, the operations may proceed to the second frame F2, and may be repeatedly performed on the frames until a desired number of pixel signals are output. FIGS. 3 and 4 illustrate only the timing diagrams of up to the second frame F2, but pixel signals for the third frame and thereafter may be successively output, for example, pixel signals may be output for 100 to 5000 frames. The output pixel signals may be converted into digital data by the data outputter 330, and may be transmitted to the processor 700.

While FIG. 3 illustrates an example in which the light source controller 500 controls the light source by using the reset signal RG among the pixel control signals, the light source controller 500 may control the light source by using another pixel control signal or the reference signal; for example, the light source controller 500 may control the light source by using the transfer signal TS among the pixel control signals, or by using the horizontal synchronization signal H-sync among the reference signals.

Hereinafter, a method of measuring blood pressure will be described as an example of analyzing bio-information by using the apparatus for measuring bio-information of FIG. 1.

Figure 5A:
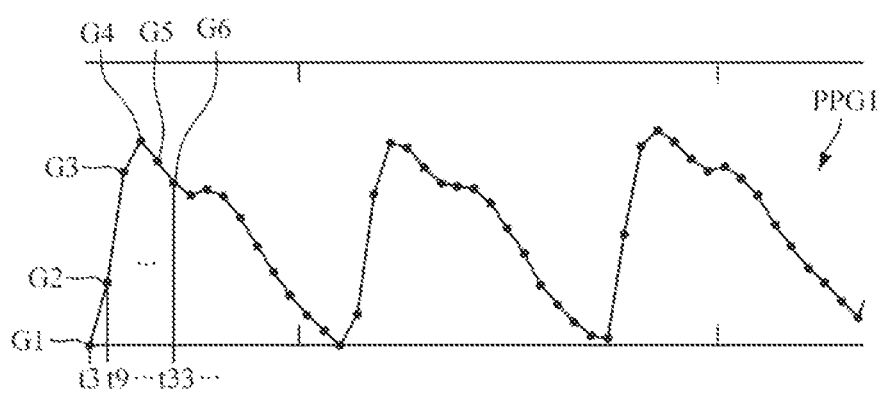
FIG. 5A is a diagram illustrating a first PPG signal for light of a first wavelength.
Figure 5B:
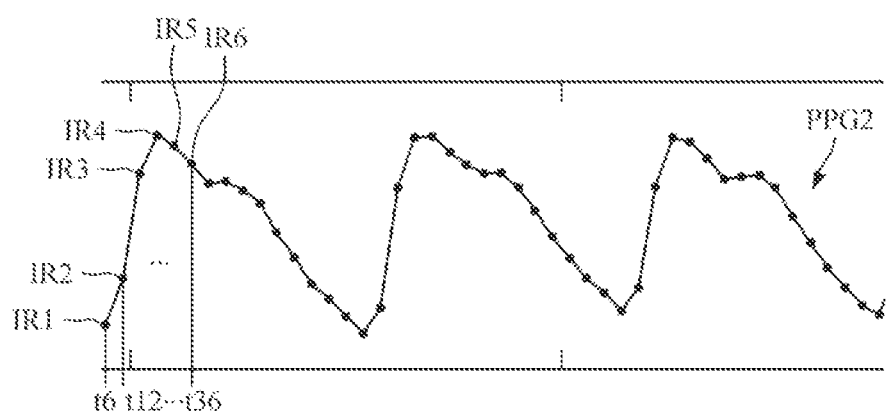
FIG. 5B is a diagram illustrating a second PPG signal for light of a second wavelength.

FIG. 5A illustrates a first PPG signal PPG1 that is obtained by using light in the first wavelength range obtained from the pixel signal of the image sensor 300, and FIG. 5B illustrates a second PPG signal PPG2 that is obtained by using light in the second wavelength range.

The Photo-plethysmography (PPG) signal may be a signal obtained by emitting light in a specific wavelength range onto a body part and detecting light reacted with the body part, and may be a signal representative of pulsation components generated by the heartbeat. The processor 700 may obtain PPG signals for light of the first and second wavelengths by using the data transmitted from the data outputter 330 of the image sensor 300.

Referring to FIGS. 5A and 5B, the respective points forming first and second PPG signals PPG1 and PPG2 may correspond to the signals sampled during the read-out operation RO of the respective pixel rows 311 to 316 as described above. For example, G1 of FIG. 5A may correspond to a pixel signal sampled from the first pixel row 311 in the third period t3 of FIG. 3; G2 may correspond to a pixel signal sampled from the third pixel row 313 in a ninth period t9; and G6 may correspond to a pixel signal sampled from the fifth pixel row 315 in a thirty-third period t33. Similarly, IR1 of FIG. 5B may correspond to a pixel signal sampled from the second pixel row 312 in a sixth period t6 of FIG. 3; IR2 may correspond to a pixel signal sampled from the fourth pixel row 314 in a twelfth period t12; and IR6 may correspond to a pixel signal sampled from the sixth pixel row 316 in a thirty-sixth period t36. The pixel signals sampled from the respective pixel rows include unit pixel signals output from the plurality of unit pixels included in the pixel row, and the processor 700 may obtain the PPG signals by processing the unit pixel signals in various manners. For example, the processor 700 may obtain a value of G1 by averaging the unit pixel signals read-out from six unit pixels included in the first pixel row 311 in the third period t3, or may obtain a value of G1 by averaging signals of only two to four unit pixels, located at a center portion, among the pixels included in the first pixel row 311. In another example, if the object OBJ is not in contact with the entire area of the pixel part 310, the bio-signal controller 700 may measure a bio-signal by using only the pixel signals of pixels being in contact with the object OBJ.

In the case where each of the G1 value, the IR1 value, and the like is defined as a bio-signal, a sampling rate (or a frame rate) of the bio-signal measured by the apparatus 1000 for measuring bio-information may be in a range of 10 Hz to 5000 Hz or 15 Hz to 1000 Hz. Therefore, the apparatus 1000 according to the embodiments of the present disclosure offers an advantage of providing a quick response time since the sampling rate (frame rate) is higher than the sample rates of conventional image sensors.

In the case where the pixel rows, performing the light exposure operation when the light emitters 100 and 120 are turned on once, are defined as one pixel region, each pixel row may indicate one pixel region in the example embodiment of FIG. 3. Two or more pixel rows may be included in one pixel region, which will be described later with reference to FIG. 9.

Figure 6:
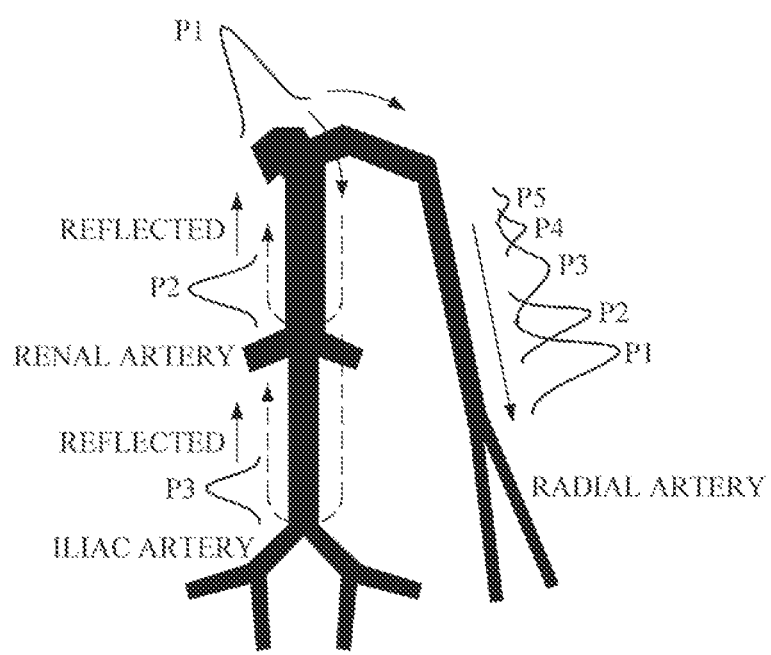
FIG. 6 is a diagram explaining a principle for generating component waveforms included in a unit waveform of a PPG signal.
Figure 7:
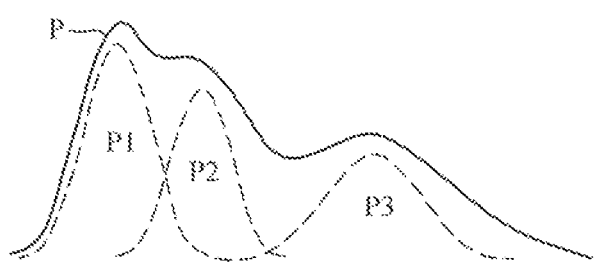
FIG. 7 is a diagram explaining component waveforms included in a unit waveform of a PPG signal.

FIG. 6 is a diagram explaining a principle for generating a unit waveform of a PPG signal, and FIG. 7 is a diagram explaining an example of dividing a unit waveform P of a PPG signal into a plurality of component waveforms.

Referring to FIGS. 6 and 7, the unit waveform P is formed by superposition of a forward wave P1, moving from the heart toward branching points of blood vessels in peripheral parts of the body such as the iliac arteries and the like, and reflected waves P2 and P3 reflected from the branching points of the peripheral parts. Specifically, component waveforms P1, P2, and P3 may include a forward wave P1 generated by contraction of the heart, a first reflected wave P2 mainly reflected from the renal arteries, and a second reflected wave P3 mainly reflected from the iliac arteries. The amplitude of the forward wave P1 is highly correlated to cardiac motility, and the reflected waves P2 and P3 are highly correlated to blood vessel characteristics. Accordingly, blood pressure may be measured by dividing the unit waveform P of the PPG signal into the respective component waveforms P1, P2, and P3 and by analyzing the intensity and duration of the respective component waveforms P1, P2 and P3, an interval between the component waveforms P1, P2, and 3, a ratio between the intensities of the component waveforms P1, P2, and P3, and the like. For example, blood pressure may be measured by analyzing a time interval between peak points of the forward wave P1 and the reflected waves P2 and P3, and/or a ratio between maximum intensities. Specifically, blood pressure may be measured by dividing the first PPG signal PPG1 of FIG. 5A and the second PPG signal PPG2 of FIG. 5B into the component waveforms P1, P2, and P3 and analyzing the component waveforms P1, P2, and P3, and by averaging these values; or based on the second PPG signal PPG2 of FIG. 5B, by using information obtained from the first PPG signal PPG1 for correcting a value obtained by analyzing the second PPG signal PPG2, accuracy in measuring blood pressure may be improved.

While FIG. 3 illustrates a method of measuring blood pressure by using light of green and infrared wavelengths, the apparatus 1000 for measuring bio-information of FIG. 1 may use light of other wavelengths, such as a blue wavelength and the like, to measure other types of bio-information, such as blood glucose, body fat, heart rate, blood oxygen saturation level, vascular compliance, blood flow rate, or arterial stiffness, and the like, in addition to blood pressure.

Figure 8:
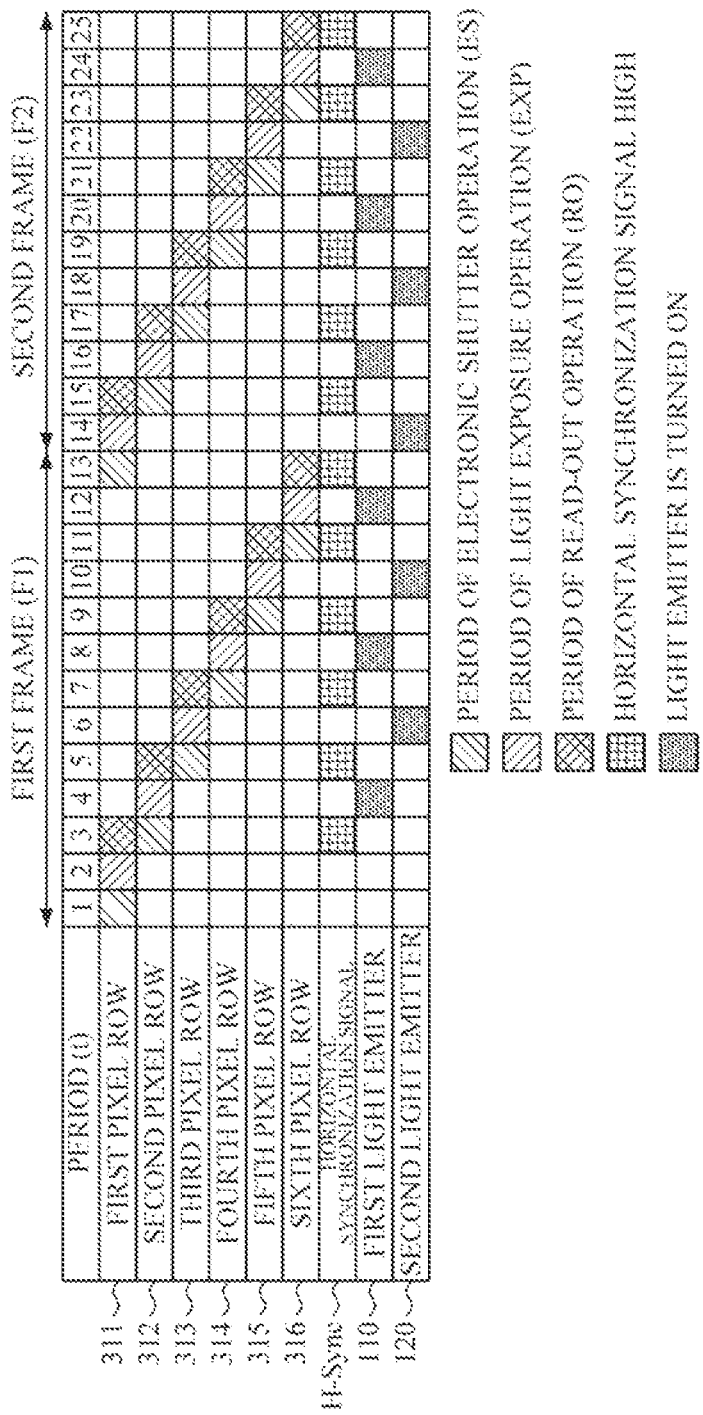
FIG. 8 is a diagram explaining an operation of an apparatus for measuring bio-information for driving a light source by using a horizontal synchronization signal.

FIG. 8 is a diagram explaining a method of driving a light source by using a horizontal synchronization signal H-sync.

The horizontal synchronization signal H-sync is a signal provided every time sampling of a pixel signal is complete for one pixel row, and may be a signal provided when the read-out operation RO of a pixel row is performed. For example, the horizontal synchronization signal H-sync may be provided in a period when the read-out operation RO is performed, such as the third period t3 in which the read-out operation RO of the first pixel row 311 is performed, the fifth period t5 in which the read-out operation RO of the second pixel row 312 is performed, and the like. Among the timing signals or the pixel control signals TG, RG, and SEL generated or used by the image sensor 300, there may be signals which are not transmitted to the outside of the image sensor 300, but in many cases the horizontal synchronization signal H-sync is transmitted to the outside through the interface of the image sensor 300, such that a method of controlling the light source based on the horizontal synchronization signal H-sync may be used effectively.

In comparison of FIG. 8 with FIG. 3, there is a difference between the example embodiment of FIG. 8 and the example embodiment of FIG. 3 in that the light source 100 is driven using the reset signal RG, among the pixel control signals TG, RG, and SEL, in the example embodiment of FIG. 3, but in the example embodiment of FIG. 8, the light source 100 is driven using the horizontal synchronization signal H-sync which is one of the timing signals. Further, there is also a difference between the example embodiment of FIG. 8 and the example embodiment of FIG. 3 in that in the example embodiment of FIG. 3, after the read-out operation RO of a preceding pixel row is performed, the electronic shutter operation ES of a subsequent pixel row is performed; by contrast, in the example embodiment of FIG. 8, the read-out operation RO of the preceding pixel row and the electronic shutter operation ES of the subsequent pixel row are performed at the same time in the same period. For example, in the example embodiment of FIG. 3, the read-out operation RO of the first pixel row 311 in the first frame F1 is performed in the third period t3, and the electronic shutter operation ES of the second pixel row 312 is performed in the fourth period t4; but in the example embodiment of FIG. 8, the electronic shutter operation ES of the second pixel row 312 may be performed in the third period t3 at the same time as the read-out operation RO of the first pixel row 311 of the first frame F1.

The light source controller 500 may control the ON/OFF of the first light emitter 110 and the second light emitter 120 by using the horizontal synchronization signal H-sync. For example, in response to the horizontal synchronization signal of the third period t3, the light source controller 500 may turn on the first light emitter 110; in response to the horizontal synchronization signal of the fifth period t5, the light source controller 500 may turn off the first light emitter 110 and may turn on the second light emitter 120. During the period of the light exposure operation EXP of the first pixel row 311 in the first frame F1 of FIG. 8, both the first and second light emitters 110 and 120 are turned off, such that the pixel signal of the first pixel row, which is read-out in the third period t3, may not be used for measuring bio-information or may be used to measure ambient light not generated by the light emitters 110 and 120. The measured ambient light which is not generated by the light emitters 110 and 120 may be used for removing noise from the signal received from the light emitters 110 and 120. Other operations in the example embodiment of FIG. 8 are similar to those described in the example embodiment of FIG. 3, such that a redundant description thereof will be omitted.

Figure 9:
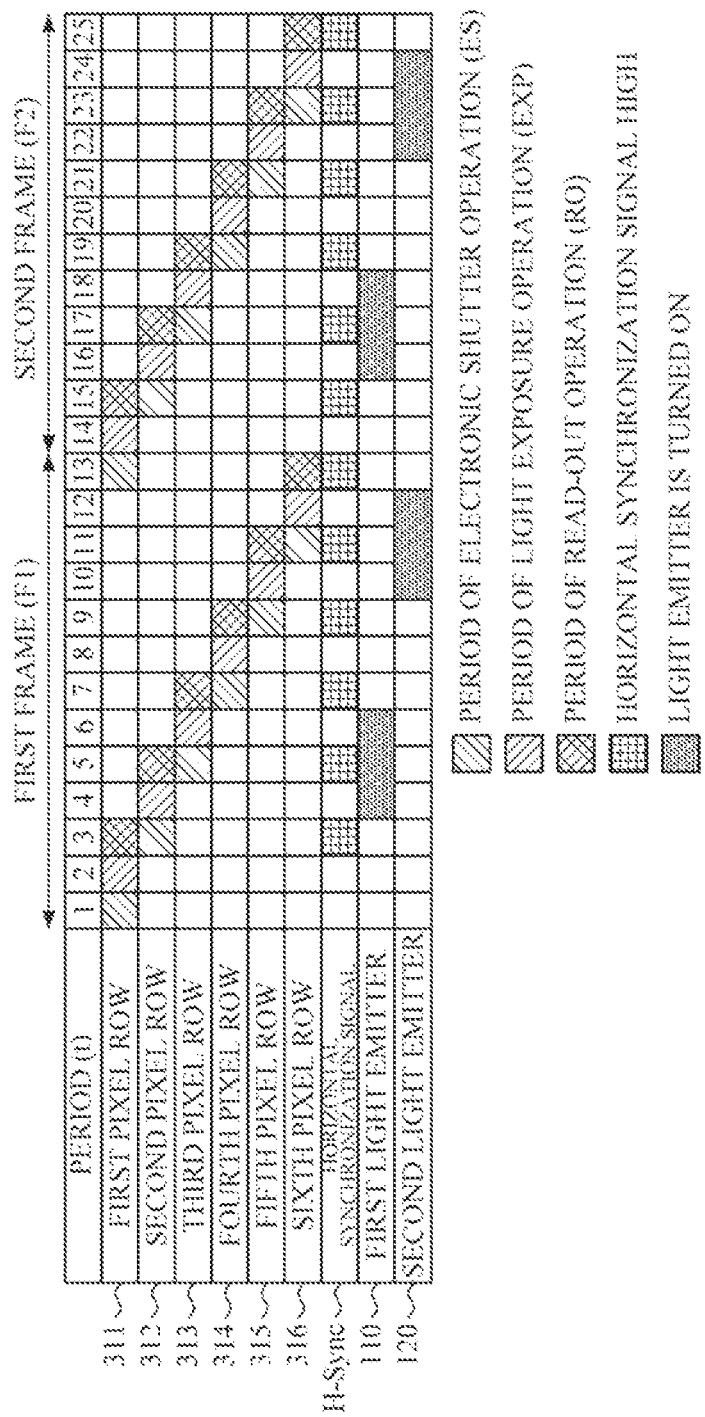
FIG. 9 is a diagram explaining an operation of an apparatus for measuring bio-information including two or more pixel rows in one pixel region.

FIG. 9 is a diagram explaining another example of a method of driving a light source by using a horizontal synchronization signal H-sync.

In comparison of FIG. 9 with FIG. 8, there is a difference in that each pixel row corresponds to one pixel region in the example embodiment of FIG. 8, but in the example embodiment of FIG. 9, two adjacent pixel rows correspond to one pixel region. As briefly described above, in the case where pixel rows, performing the light exposure operation when the light emitters 110 and 120 are turned on once, are defined as a pixel region, the second and third pixel rows 311 and 312, performing the light exposure operation EXP in the fourth to sixth periods t4 to 46 when the first light emitter 110 of FIG. 9 is turned on, may correspond to one pixel region. Similarly, the fifth and sixth pixel rows 315 and 316, performing the light exposure operation EXP in the tenth to twelfth periods t10 to t12 when the second light emitter 120 is turned on, may correspond to one pixel region.

The pixel signal, output from one pixel region, may be treated as one signal for analyzing a bio-signal. For example, an average sample value, obtained by averaging a value sampled from the second pixel row 312 in the fifth period t5 of the first frame F1 of FIG. 9 and a sample value sampled from the third pixel row 313 in the seventh period t7, may be used for measuring bio-information. However, the pixel signals output from the first and fourth pixel rows 311 and 314 of the first frame F1 of FIG. 9, which perform the light exposure operation EXP only in a period when both the light emitters 110 and 120 are turned off, may not be used for measuring bio-information. For example, the pixel signal of the first pixel row 311, which is sampled in the third period t3, and the pixel signal of the fourth pixel row 314 which is sampled in the ninth period t9, may not be used for measuring bio-information. As described above, by placing pixel rows, on which sampling of pixel signals is not performed, between a pixel region on which sampling of bio-information obtained using the first light emitter 110 is performed and a pixel region on which sampling of bio-information obtained using the second light emitter 120 is performed, it is possible to reduce noise occurring due to a turn-off delay of the light emitters. For example, the first light emitter 110 is required to be turned off immediately by the horizontal synchronization signal H-sync of the seventh period t7 of FIG. 9, but a turn-off timing is delayed such that the first light emitter 110 is maintained in an ON state until the eighth period t8, in which the fourth pixel row 314 performs the light exposure operation. Even in this case, bio-information obtained using the second light emitter 120 is sampled not starting from the eighth period t8 but from the tenth period t10, thereby preventing noise which occurs due to the turn-off delay of the first light emitter 110.

The light source controller 500 of FIG. 9 may control the ON/OFF of the first and second light emitters 110 and 120 by using the horizontal synchronization signal H-sync. For example, the light source controller 500 may turn on the first light emitter 110 in response to the horizontal synchronization signal H-sync of the third period t3, and may turn off the first light emitter 110 in response to the horizontal synchronization signal H-sync of the seventh period t7. In addition, the light source controller 500 may turn on the second light emitter 120 in response to the horizontal synchronization signal H-sync of the ninth period t9, and may turn off the second light emitter 120 in response to the horizontal synchronization signal H-sync of the thirteenth period t13.

While the example embodiment of FIG. 9 illustrates an example in which two pixel rows are included in one pixel region, the number of pixel rows included in one pixel region may be three or more, or may be 10 to 500 or 10 to 100.

Figure 10:
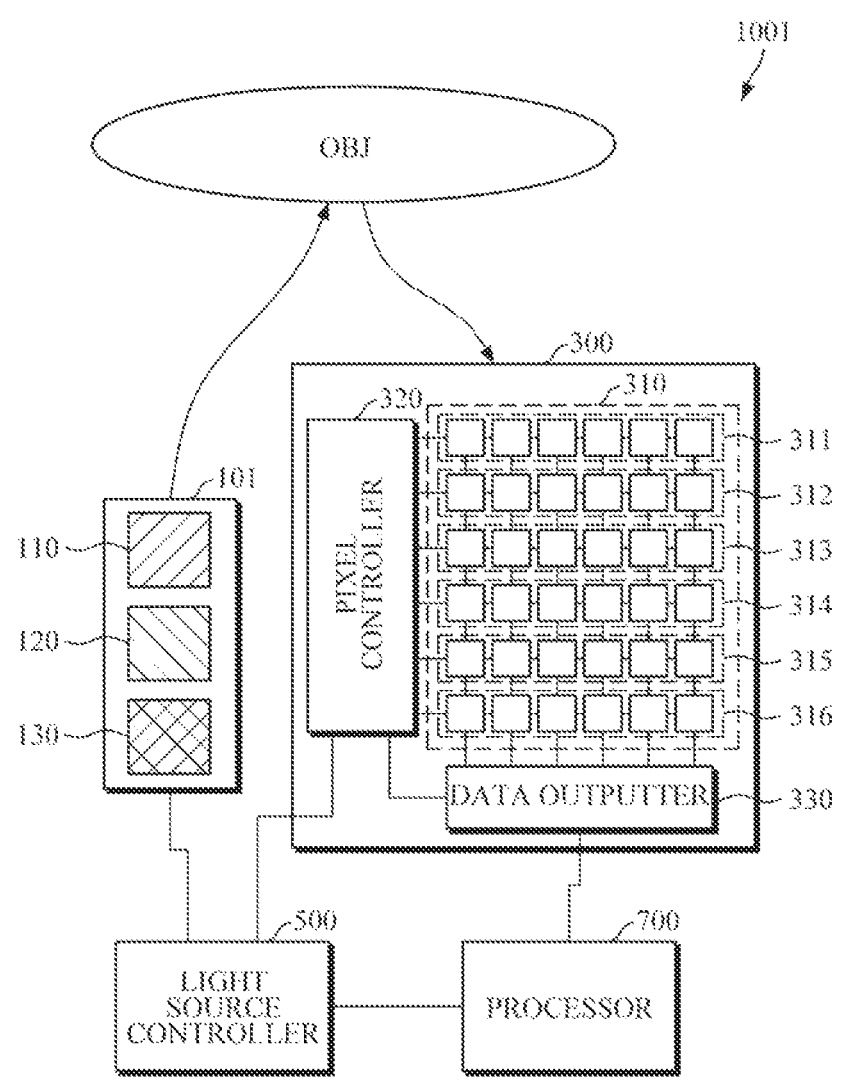
FIG. 10 is a block diagram illustrating an apparatus for measuring bio-information including a third light emitter.
Figure 11:
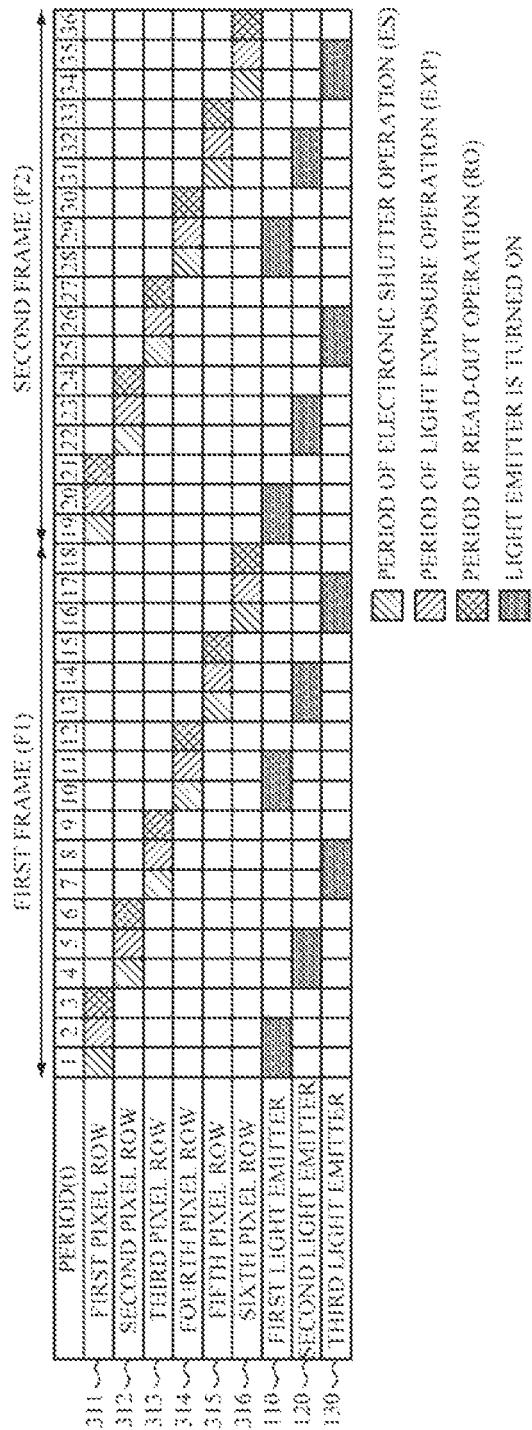
FIG. 11 is a diagram explaining operations of a pixel part and a light source of the apparatus for measuring bio-information of FIG. 10.

FIG. 10 is a schematic diagram illustrating an example of a structure of an apparatus for measuring bio-information which includes three light emitters, and FIG. 11 is a diagram explaining an operation of a pixel part and a light source of FIG. 10.

In comparison of FIG. 10 with FIG. 1, there is a difference between a light source 101 of FIG. 10 and the light source 100 of FIG. 1 in that the light source 101 of FIG. 10 further includes a third light emitter 130. The third light emitter 130 may emit light of a third wavelength, e.g., a red wavelength (in a range of 625 nm to 740 nm), which is different from the wavelengths of the light emitted from the first and second light emitters 110 and 120.

Referring to FIG. 11, a light source controller 500 of FIG. 10 may sequentially drive the first to third light emitters 110, 120, and 130; for example, the light source controller 500 may turn on the first light emitter 110 in the first and second periods t1 and t2, may turn on the second light emitter 120 in the fourth and fifth periods t4 and t5, and may turn on the third light emitter 130 in the seventh and eighth periods t7 and t8. The apparatus 1001 for measuring bio-information of FIG. 10 may measure bio-information by analyzing a bio-signal for the light having the third wavelength.

While FIG. 10 illustrates an example of a structure including three light emitters 110, 120, and 130 emitting light of three different wavelengths, four or more light emitters emitting light of four or more wavelengths, for example, four to nine light emitters may be included.

Figure 12:
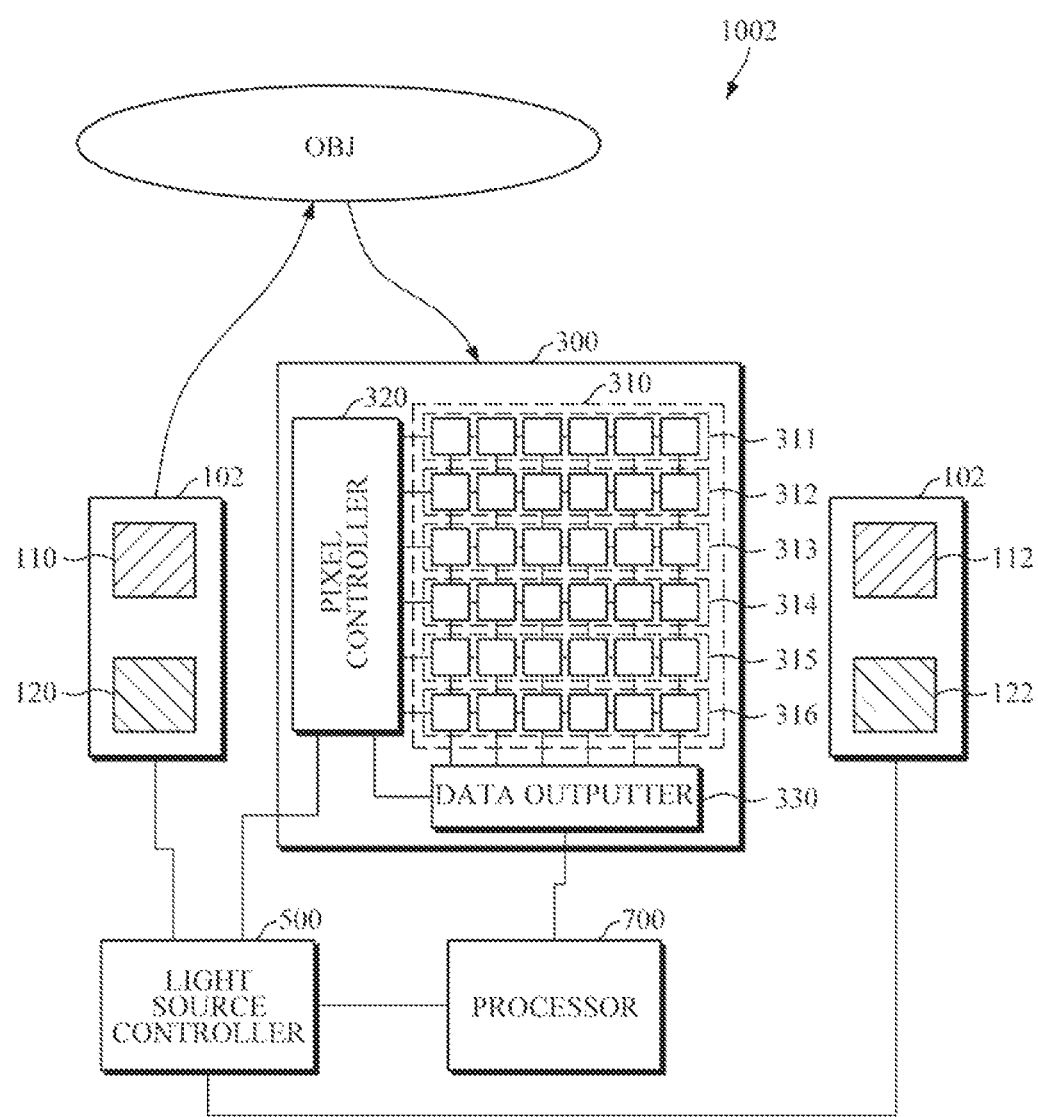
FIG. 12 is a block diagram illustrating an apparatus for measuring bio-information including two or more light emitters emitting light of the same wavelength.
Figure 13B:
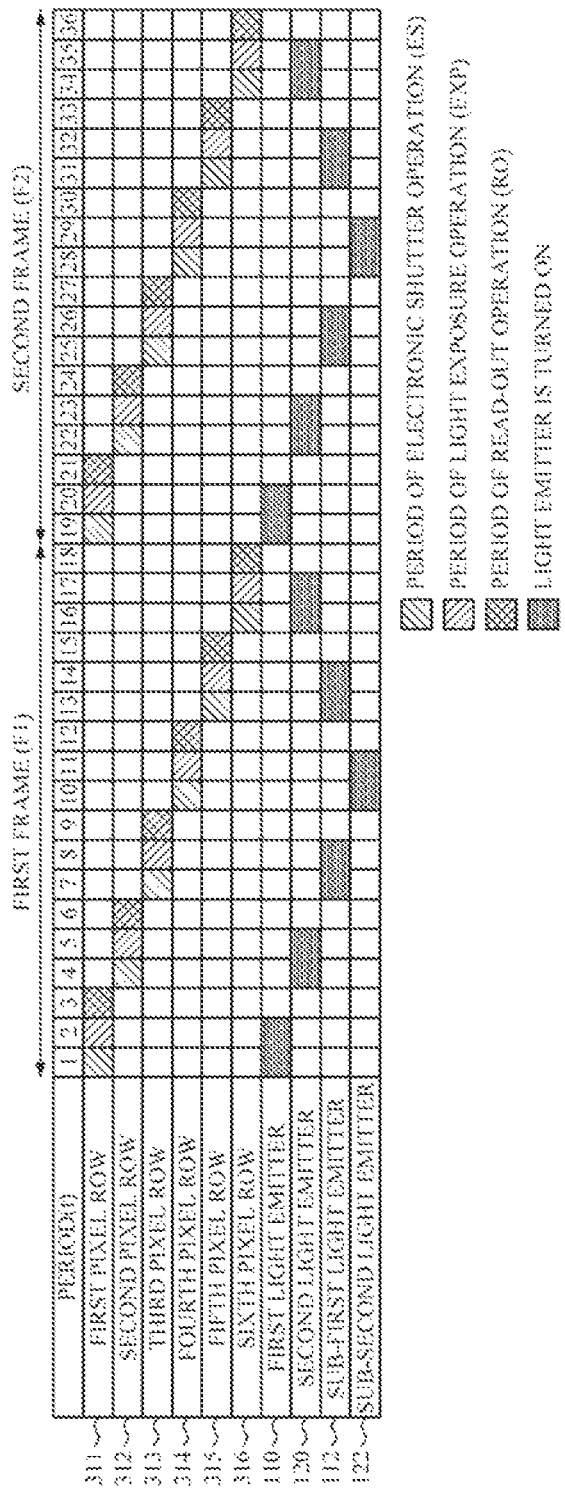
FIG. 13B is a diagram explaining another example of a method of driving a light source of FIG. 12.

FIG. 12 is a schematic diagram illustrating a structure of an apparatus for measuring bio-information including two or more light emitters emitting light of the same wavelength; and FIGS. 13A and 13B are diagrams explaining operations of a pixel part and a light source of FIG. 12.

In comparison of FIG. 12 with FIG. 1, a light source 102 of FIG. 12 is different from the light source 100 of FIG. 1 in that the light source 102 of FIG. 12 further includes a sub-first light emitter 112 emitting light of the first wavelength, and a sub-second light emitter 122 emitting light of the second wavelength. The wavelength of the light emitted from sub-first light emitter 112 may be the same or substantially the same as the wavelength of the light emitted from the first light emitter 110. The wavelength of the light emitted from sub-second light emitter 122 may be the same or substantially the same as the wavelength of the light emitted from the second light emitter 120. In the light source 102 of FIG. 12, the light emitters 110, 120, 112, and 122 emitting light are disposed on both sides of the image sensor 300, such that it is possible to control a deviation of the amount of the emitted light, which occurs in the distance between the light emitters 110, 120, 112, and 122 and the pixels.

Referring to FIG. 13A, a light source controller 500 of FIG. 12 may control the sub-first light emitter 112 to be turned on/off at the same time as the first light emitter 110, and may control the sub-second light emitter 122 to be turned on/off at the same time as the second light emitter 120. The light source controller 500 may synchronize the turned on time of the sub-first light emitter 112 and the first light emitter 110, and may synchronize the turned on time of the sub-second light emitter 122 and the second light emitter 120. For example, the light source controller 500 may control the first light emitter 110 and the sub-first light emitter 112 to be turned on at the same time in the first and second periods t1 and t2, and may control the second light emitter 120 and the sub-second light emitter 122 to be turned on at the same time in the fourth and fifth periods t4 and t5.

Referring to FIG. 13B, the light source controller 500 of FIG. 12 may control the first light emitter 110 and the sub-first light emitter 112 to be turned on and off alternately, and may control the second light emitter 120 and the sub-second light emitter 122 to be turned on and off alternately. For example, the light source controller 500 may control only the first light emitter 110 to be turned on in the first and second periods t1 and t2, and may control only the sub-first light emitter 112 to be turned on in the seventh and eighth periods t7 and t8.

While FIG. 12 illustrates an example in which the light source 102 includes two light emitters emitting light of the same wavelength, the light sources emitting light of the same wavelength may be two or more, e.g., three to eight in number.

Figure 14A:
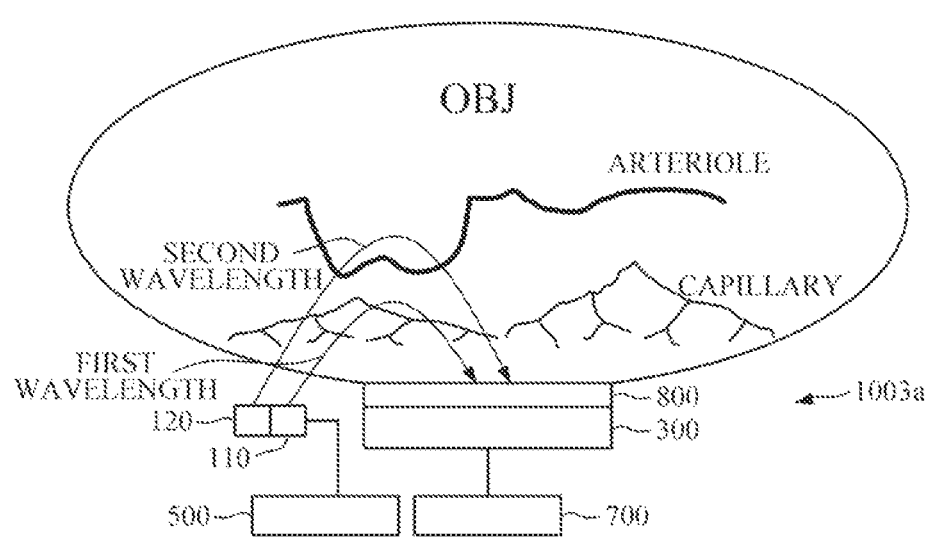
FIG. 14A is a block diagram illustrating an apparatus for measuring bio-information including a force sensor disposed above an image sensor.
Figure 14B:
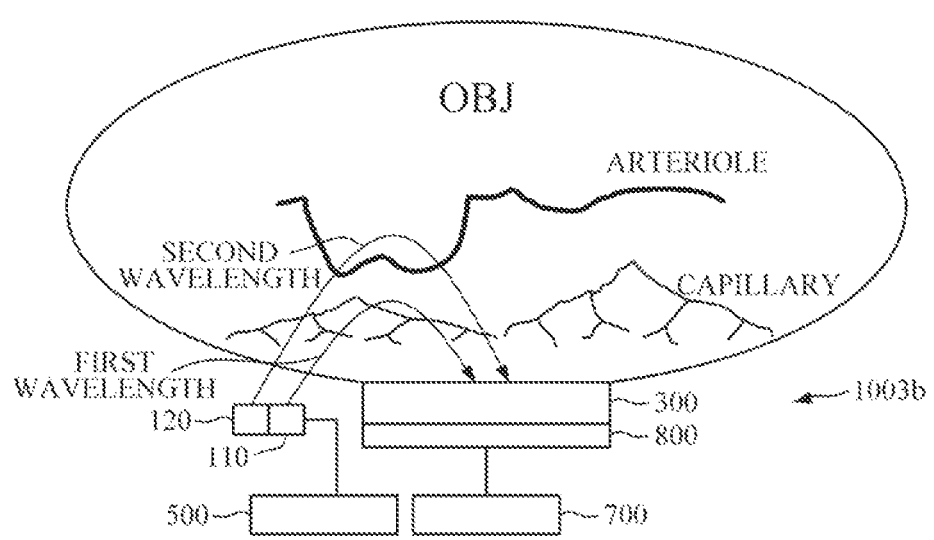
FIG. 14B is a diagram illustrating an apparatus for measuring bio-information including a force sensor disposed below an image sensor.

FIGS. 14A and 14B are schematic diagrams illustrating a structure of an apparatus for measuring bio-information which further includes a force sensor.

In comparison of FIGS. 14A and 14B with FIG. 1, the apparatus for measuring bio-information of FIGS. 14A and 14B may further include a force sensor disposed on the top or bottom of an image sensor.

A force sensor 800 may be disposed on the top of the image sensor 300 as illustrated in FIG. 14A or may be disposed on the bottom of the image sensor 330 as illustrated in FIG. 14B, and may measure the intensity of a pressing force of the object OBJ. The force sensor 800 may be a voltage resistive sensor, an ultrasonic force sensor, a load cell sensor, a capacitive force sensor, a pyroelectric force sensor, a strain gauge force sensor, an electrochemical force sensor, an optical force sensor, or a magnetic force sensor.

Apparatuses 1003a and 1003b for measuring bio-information of FIGS. 14A and 14B may measure bio-information by combining information, provided by the force sensor 800, with information provided by the image sensor 300. Hereinafter, a method of measuring blood pressure by the apparatus 1003a for measuring bio-information of FIG. 14A will be described with reference to FIGS. 15A, 15B, and 16.

Figure 15A:
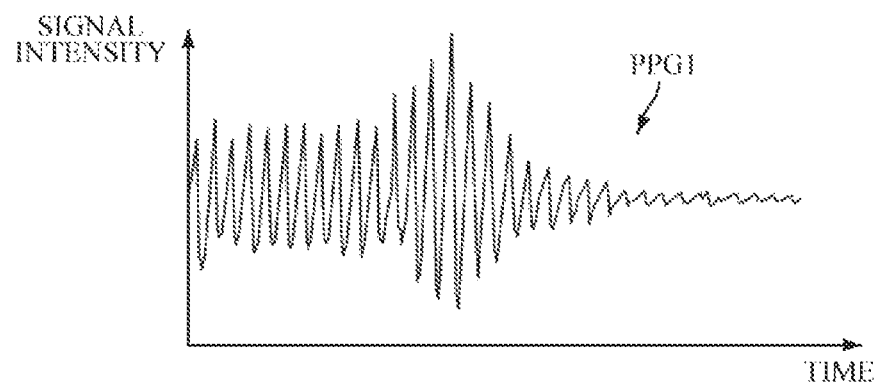
FIGS. 15A and 15B are diagrams illustrating a PPG signal measured using the image sensor of FIG. 14A.
Figure 15B:
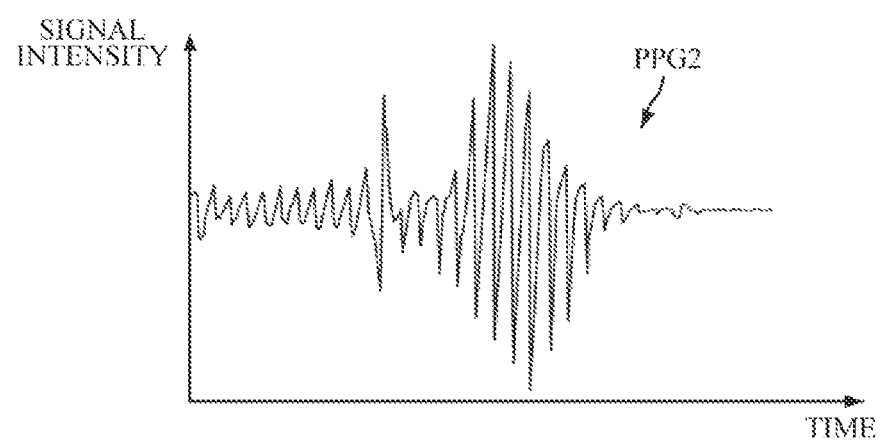
Figure 15C:
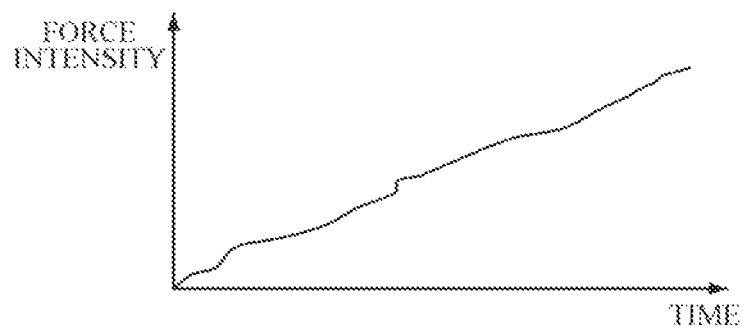
FIG. 15C is a diagram illustrating a force intensity measured using a force sensor of FIG. 14A.

FIGS. 15A and 15B are diagrams illustrating PPG signals PPG1 and PPG2 measured by the image sensor 300 when the object OBJ presses the force sensor 800 of FIG. 14A by gradually increasing a pressing force, and FIG. 15C is a diagram illustrating the intensity of a pressing force measured by the force sensor 800.

FIG. 15A illustrates the first PPG signal PPG1 obtained for light of the first wavelength, and FIG. 15B illustrates the second PPG signal PPG2 obtained for light of the second wavelength. The light of the first wavelength, which is a short wavelength, may not penetrate deep into the skin, such that the first PPG signal PPG1 may include a signal reflected from the capillary. By contrast, the light of the second wavelength, which is a long wavelength, may penetrate into the arteriole located at a greater depth than the capillary, such that the second PPG signal PPG2 may include signals from both the capillary and the arteriole. As information related to blood pressure is included more in the signal of the arteriole than the signal of the capillary, such that the signal of the arteriole may be obtained by removing the signal of the capillary from the second PPG signal PPG2; and the first PPG signal PPG1 may be used for removing the signal of the arteriole from the second PPG signal PPG2.

FIG. 15C illustrates a value measured when the object OBJ presses the force sensor by gradually increasing a pressing force, and it can be seen that the pressing force gradually increases with time.

Figure 16:
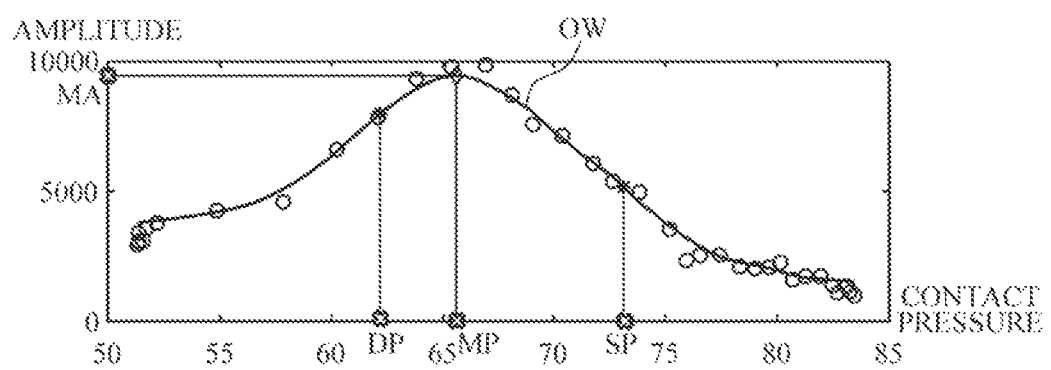
FIG. 16 is a diagram illustrating an oscillometric envelope obtained using data illustrated in FIGS. 15A to 15C.

The processor 700 may normalize the first and second PPG signals PPG1 and PPG2 to obtain second-order differential signals thereof, and may normalize again the second-order differential signals and subtract the second-order differential signal of the first PPG signal PPG1 from the second-order differential signal of the second PPG signal PPG2 to obtain a subtracted differential signal. An oscillometric waveform envelope OW as illustrated in FIG. 16 may be obtained by extracting a peak-to-peak point by using a waveform envelope of the subtracted differential signal, and by plotting the peak-to-peak amplitude against the intensity of the force. However, the example embodiment is not limited to the second-order differential signal, and the oscillometric waveform envelope OW may also be obtained by using the first and second PPG signals PPG1 and PPG2. A force intensity at a maximum peak point may be calculated as mean arterial pressure (MAP), and force intensities SP and DP, located at the right and left points of the maximum peak point and having a preset ratio to the force intensity at the maximum peak point, may be calculated as systolic blood pressure SBP and diastolic blood pressure DBP, respectively.

Figure 17:
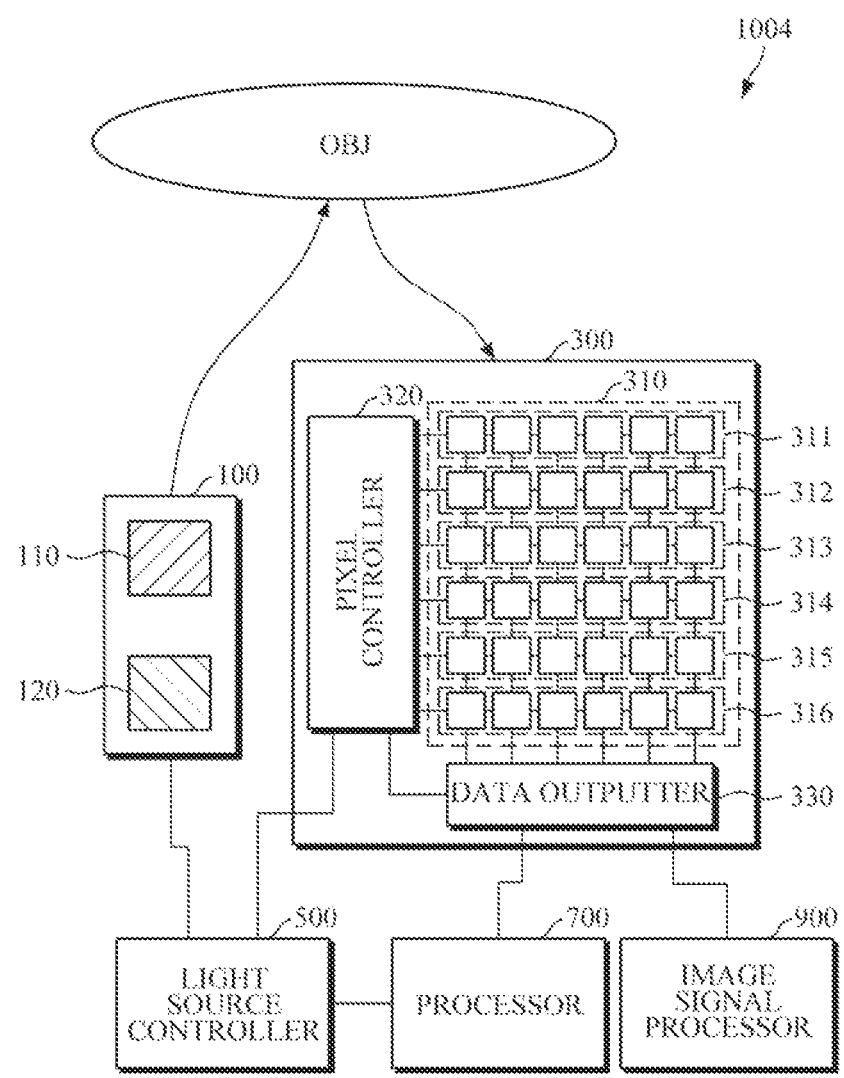
FIG. 17 is a block diagram illustrating an apparatus for measuring bio-information including an image signal processor.

FIG. 17 is a schematic diagram illustrating a structure of an apparatus for measuring bio-information which includes an image signal processor.

An image signal processor 900 may receive a pixel signal of the image sensor 300 to generate image information, and the image information may be used in various manners for measuring bio-information. The image signal processor 900 may be implemented by using a graphics processing unit (GPU), and may be integrated into the processor 700 or embodied as a separate chip or element from the processor 700. For example, the image information may include information on a contact area between the object OBJ and the image sensor 300, and may be used to calculate pressure applied by the object OBJ based on the contact area between the object OBJ and the image sensor 300 and the intensity of the pressing force of the object OBJ, and the calculated pressure may be used to measure blood pressure. In another example, the image information may be used to determine whether the object OBJ is in contact with, or is close to, the apparatus for measuring bio-information in a manner sufficient to measure bio-information, and the apparatus for measuring bio-information may be maintained in a standby state, without performing measurement, until the object OBJ is located within a distance where bio-information may be measured. In yet another example, in the case where the object OBJ is required to be located in a correct position to measure bio-information, the apparatus for measuring bio-information may determine a current position of the object OBJ, and may provide information on a direction for a user to move the object OBJ.

Figure 18:
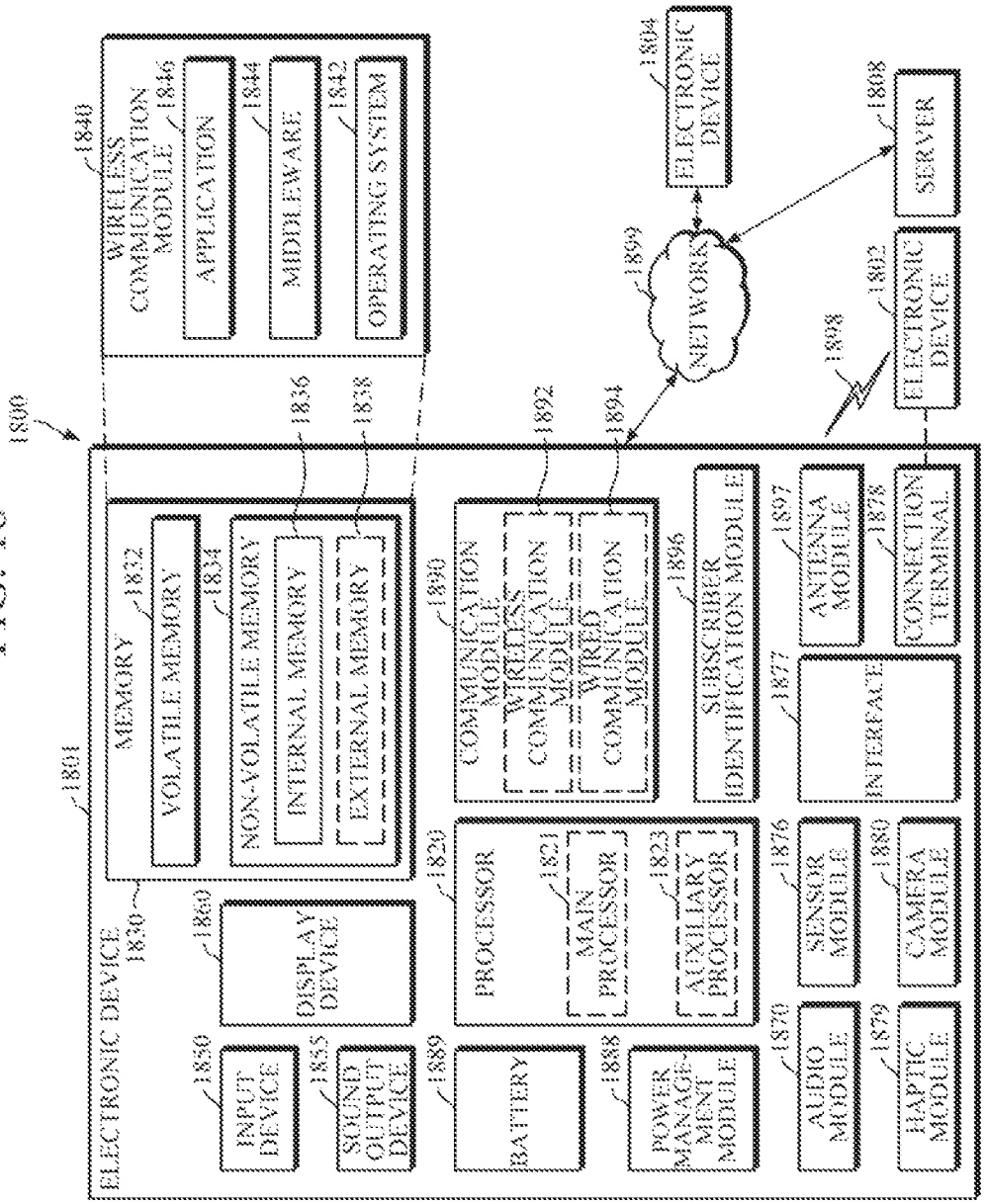
FIG. 18 is a block diagram illustrating an electronic device including an apparatus for measuring bio-information.

FIG. 18 is a block diagram of an electronic device including an apparatus for measuring bio-information.

The electronic device 1801 includes a processor 1820, a memory 1830, an input device 1850, a sound output device 1855, a display device 1860, an audio module 1870, a sensor module 1876, an interface 1877, a haptic module 1879, a camera module 1880, a power management module 1888, a battery 1889, a communication module 1890, a subscriber identification module 1896, and/or an antenna module 1897. In some embodiments, at least one of the components (e.g., display device 1860, etc.) may be omitted from the electronic device 1801, and one or more other components may be added in the electronic device 1801. The aforementioned apparatuses 1000, 1001, 1002, 1003a, 1003b, and 1004 for measuring bio-information illustrated in FIGS. 1, 10, 12, 14A, 14B, and 17 may be implemented as single integrated circuitry to be mounted in the sensor module 1876 of the electronic device 1801, or may be distributed in different components. For example, the image sensor 300 and/or the light source 100 may be included in the sensor module 1876, and the light source controller 500, the processor 700, and/or the image signal processor 900 may be included in the processor 1820.

The processor 1820 may execute, for example, software (e.g., a program 1840, etc.) to control at least one or more other components (e.g., a hardware or software component, etc.) of the electronic device 1801 connected to the processor 1820, and may perform various data processing or computation. According to an example embodiment, as part of the data processing or computation, the processor 1820 may load a command or data received from another component (e.g., the sensor module 1876, the communication module 1890, etc.) in a volatile memory 1832, process the command or the data stored in the volatile memory 1832, and store resulting data in a non-volatile memory 1834. The processor 1820 may generate a master clock for synchronization of operations of the components, and may provide the master clock to, for example, the pixel controller 320 of FIGS. 1, 10, 12, 14A, 14B, and 17 described above.

The processor 1820 may include a main processor 1821 (e.g., a central processing unit (CPU) or an application processor (AP), etc.), and an auxiliary processor 1823 (e.g., a graphics processing unit (GPU), an image signal processor (ISP), a sensor hub processor, or a communication processor (CP), etc.) that is operable independently from, or in conjunction with, the main processor 1821. The auxiliary processor 1823 may be adapted to consume less power than the main processor 1821, or to be specific to a specified function. The auxiliary processor 1823 may control at least some of functions or states related to at least one component (e.g., the display device 1860, the sensor module 1876, the communication module 1890, etc.) among the components of the electronic device 1801, instead of the main processor 1821 while the main processor 1821 is in an inactive state (e.g., sleep state), or together with the main processor 1821 while the main processor is in an active state (e.g., application execution state). The auxiliary processor 1823 (e.g., an image signal processor, a communication processor, etc.) may be implemented as part of another component (e.g., the camera module 1880, the communication module 1890, etc.) functionally related to the auxiliary processor 1823.

In response to a user's request for measuring bio-information, the processor 1820 may transmit a control signal to the image sensor 300, the light source controller 500, the processor 700, and/or the image signal processor 900 of the aforementioned apparatuses 1000, 1001, 1002, 1003a, 1003b, and 1004. The light source controller 500, the processor 700, and/or the image signal processor 900 may be implemented as independent processors, or may be integrated into the main processor 1821 or the auxiliary processor 1823 of the electronic device 1801.

The memory 1830 may store various data required for at least one component (e.g., the processor 1820, the sensor module 1876, etc.) of the electronic device 1801. The various data may include, for example, software (e.g., the program 1840, etc.) and input data or output data for a command related thereto. The memory 1830 may include a volatile memory 1832 and/or a non-volatile memory 1834.

The program 1840 may be stored as software in the memory 1830, and may include, for example, an operation system (OS) 1842, middleware 1844, and/or an application 1846.

The input device 1850 may receive a command or data to be used by another component (e.g., the processor 1820, etc.) of the electronic device 1801, from an external source (e.g., a user, etc.) of the electronic device 1801. The input device 1850 may include, for example, a microphone, a mouse, a keyboard, or a digital pen (e.g., a stylus pen, etc.).

The sound output device 1855 may output sound signals to the outside of the electronic device 1801. The sound output device 1855 may include, for example, a speaker and/or a receiver. The speaker may be used for general purposes, such as playing multimedia or playing record, and the receiver may be used for incoming calls. The receiver may be implemented separately from, or as part of, the speaker.

The display device 1860 may visually provide information to the outside of the electronic device 1801. The display device 1860 may include, for example, a display, a hologram device, or a projector and control circuitry to control a corresponding one of the display, hologram device, and projector. The display device 1860 may include touch circuity adapted to detect a touch, and/or sensor circuitry (e.g., pressure sensor, etc.) adapted to measure the intensity of force incurred by the touch.

The audio module 1870 may convert a sound into an electrical signal or vice versa. The audio module 1870 may obtain the sound via the input device 1850, or may output the sound via the sound output device and/or a headphone of an external electronic device (e.g., electronic device 1802, etc.) directly or wirelessly connected to the electronic device 1801.

The sensor module 1876 may detect an operating state (e.g., power, temperature, etc.) of the electronic device 1801 or an external environment state (e.g., a state of a user, etc.), and may generate an electrical signal or a data value corresponding to the detected state. The sensor module 1876 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor. The aforementioned apparatuses 1000, 1001, 1002, 1003$a$, 1003$b$, and 1004 of FIGS. 1, 10, 12, 14A, 14B, and 17 may be one of biometric sensors included in the sensor module 1876.

The interface 1877 may support one or more specified protocols used by the electronic device 1801 to be directly or wirelessly connected to other electronic device (e.g., electronic device 1802, etc.). The interface 1877 may include, for example, a high definition multimedia interface (HDMI), a universal serial bus (USB) interface, a secure digital (SD) card interface, and/or an audio interface.

A connecting terminal 1878 may include a connector via which the electronic device 1801 may be physically connected to the external electronic device (e.g., electronic device 1802, etc.). The connecting terminal 1878 may include, for example, a HDMI connector, a USB connector, a SD card connector, and/or an audio connector (e.g., headphone connector, etc.).

A haptic module 1879 may convert an electrical signal into a mechanical stimulus (e.g., vibration, motion, etc.) or electrical stimulus which may be recognized by a user by tactile sensation or kinesthetic sensation. The haptic module 1879 may include, for example, a motor, a piezoelectric element, and/or an electric stimulator.

The camera module 1880 may capture still images or moving images. The camera module 1880 may include a lens assembly having one mor more lenses, image sensors, image signal processors, and/or flashes. The lens assembly included in the camera module 1880 may collect light emanating from a subject to be imaged.

The power management module 1888 may manage power supplied to the electronic device 1801. The power management module 1888 may be implemented as least part of, for example, a power management integrated circuit (PMIC).

The battery 1889 may supply power to at least one component of the electronic device 1801. The battery 1889 may include, for example, a primary cell which is not rechargeable, a secondary cell which is rechargeable, or a fuel cell.

The communication module 1890 may support establishment of a direct (e.g., wired) communication channel and/or a wireless communication channel between the electronic device 1801 and other electronic device (e.g., the electronic device 1802, the electronic device 1804, the server 1808, etc.) within a network environment 1800, and performing of communication via the established communication channel. The communication module 1890 may include one or more communication processors that are operable independently from the processor 1820 (e.g., an application processor, etc.) and supports a direct communication and/or a wireless communication. The communication module 1890 may include a wireless communication module 1892 (e.g., a cellular communication module, a short-range wireless communication module, or a global navigation satellite system (GNSS) communication module) and/or a wired communication module (e.g., a local area network (LAN) communication module, a power line communication (PLC) module, etc.). Among these communication modules, a corresponding communication module may communicate with other electronic device via a first network 1898 (e.g., a short-range communication network, such as Bluetooth™, Wi-Fi direct, or infrared data association (IrDA)) or a second network 1899 (e.g., a long-range communication network, such as a cellular network, the Internet, or a computer network (e.g., LAN, wide area network (WAN), etc.). These various types of communication modules may be implemented as a single component (e.g., a single chip, etc.), or may be implemented as multi components (e.g., multi chips) separate from each other. The wireless communication module 1892 may identify and authenticate the electronic device 1801 in a communication network, such as the first network 1898 or the second network 1899, using subscriber information (e.g., international mobile subscriber identity (IMSI), etc.) stored in the subscriber identification module 1896.

The antenna module 1897 may transmit or receive a signal and/or power to or from an external device (e.g., other electronic device, etc.). The antenna module 1897 may include an antenna including a radiating element formed of a conductive pattern formed on a substrate (e.g., PCB, etc.). The antenna module 1897 may include one or a plurality of antennas. In the case where the antenna module 1897 includes a plurality of antennas, at least one antenna appropriate for a communication scheme used in the communication network, such as the first network 1898 and/or the second network 1899, may be selected from among the plurality of antennas by the communication module 1890. Signals or power may be transmitted or received between the communication module and other electronic device via the selected antenna. In addition to the antenna, other component (e.g., a radio frequency integrated circuit (RFIC), etc.) may be further included as part of the antenna module 1897.

At least some of the above-described components may be mutually connected and may communicate signals (e.g., commands, data, etc.) therebetween via an inter-peripheral communication scheme (e.g., bus, general purpose input and output (GPIO), serial peripheral interface (SPI), mobile industry processor interface (MIPI), etc.).

Commands or data may be transmitted or received between the electronic device 1801 and the external electronic device 1804 via the server 1808 connected to the second network 1899. Other electronic devices 1802 and 1804 may be a device of a same type as, or a different type from, the electronic device 1801. All of some of operations to be executed at the electronic device 1801 may be executed at one or more of other electronic devices 1802, 1804, and 1808. For example, if the electronic device 1801 is required to perform a function or a service automatically, the electronic device 1801, instead of executing the function or the service, may request the one or more other electronic devices to perform at least part of the function or the service. The one or more other electronic devices, which receives the request, may perform at least part of the function or the service requested, or an additional function or an additional service related to the request, and may transmit a result of the performed function or service to the electronic device 1801. To this end, a cloud computing, distributed computing, and/or client-server computing technology may be used.

Figure 19:
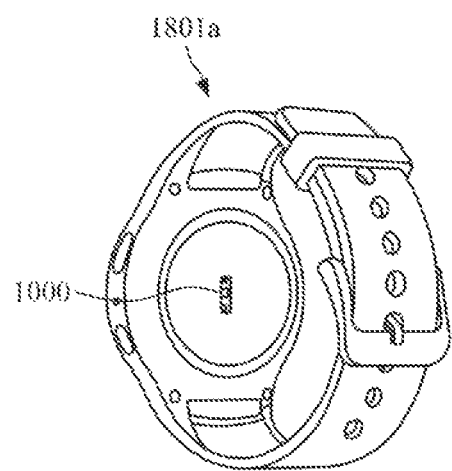
FIG. 19 is a diagram illustrating an example of a wristwatch-type electronic device including an apparatus for measuring bio-information.
Figure 20:
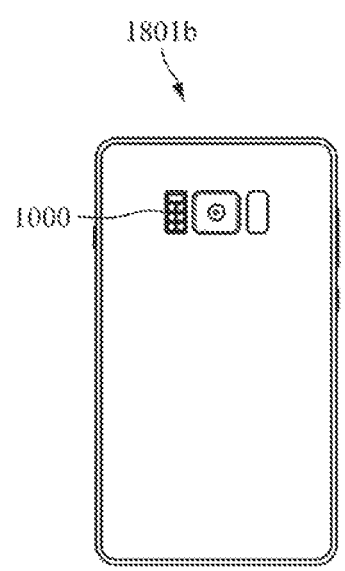
FIG. 20 is a diagram illustrating an example of a mobile electronic device including an apparatus for measuring bio-information.
Figure 21:
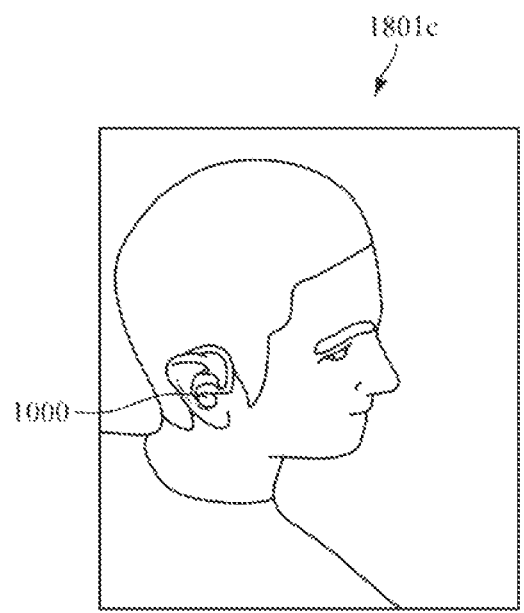
FIG. 21 is a diagram illustrating an example of an ear wearable device including an apparatus for measuring bio-information.

FIGS. 19 to 21 are diagrams illustrating examples of an electronic device having an apparatus for measuring bio-information mounted therein.

Referring to FIG. 19, the electronic device 1801 of FIG. 18 may be implemented as a wristwatch-type wearable device 1801*a*, and may include a main body and a wrist strap. A display is provided on a front surface of the main body, and may display various application screens, including time information, received message information, and the like. The apparatuses 1000, 1001, 1002, 1003*a*, 1003*b*, and 1004 for measuring bio-information may be disposed on a rear surface of the main body. The apparatuses 1000, 1001, 1002, 1003*a*, 1003*b*, and 1004 for measuring bio-information may output optical signals to a body part, such as a user's wrist, which comes into contact with the rear surface of the main body, and may measure bio-signals by detecting reflected light. By analyzing the bio-signals measured by the apparatuses 1000, 1001, 1002, 1003*a*, 1003*b*, and 1004 for measuring bio-information, the electronic device 1801*a* may measure a user's bio-information such as blood pressure, vascular age, arterial stiffness, aortic pressure waveform, stress index, and the like.

Referring to FIG. 20, the electronic device 1801 of FIG. 18 may be implemented as a mobile device 1801*b* such as a smartphone, and may include a housing and a display panel.

The housing may form an exterior of the electronic device 1801*b*. The housing has a first surface, a second surface facing the first surface, and a side surface surrounding a space between the first surface and the second surface. A display panel and a cover glass may be disposed sequentially on the first surface of the housing, and the display panel may be exposed to the outside through the cover glass. The apparatuses 1000, 1001, 1002, 1003*a*, 1003*b*, and 1004 for measuring bio-information, the camera module, and the infrared sensor may be disposed on the second surface of the housing. When a user transmits a request for bio-information by executing an application stored in the electronic device 1801*b*, the electronic device 1801*b* may measure bio-information by using the apparatuses 1000, 1001, 1002, 1003*a*, 1003*b*, and 1004 for measuring bio-information, and may provide the measured bio-information as images and/or sounds to a user.

Referring to FIG. 21, the electronic device 1801 of FIG. 18 may be implemented as an ear wearable device 1801*c*, and may include a main body and an ear strap.

A user may wear the electronic device 1801*c* of FIG. 21 by hanging the ear strap on a user's auricle, and the main body may be inserted into the external auditory meatus. The apparatuses 1000, 1001, 1002, 1003*a*, 1003*b*, and 1004 for measuring bio-information may be mounted in the main body, and may output optical signals to a body part, such as the wall of external auditory meatus, which comes into contact with the main body, and may measure bio-signals by detecting reflected light. The electronic device 1801*c* of FIG. 21 may provide the bio-information, measured by the apparatuses 1000, 1001, 1002, 1003*a*, 1003*b*, and 1004 for measuring bio-information, as sounds to a user, or may transmit the measured bio-information to an external device (e.g., mobile device, tablet PC, etc.) through a communication module mounted in the main body.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing example embodiments are merely examples and are not to be construed as liming the present disclosure. The description of the example embodiments is intended to be illustrative, and not to limit the scope of the disclosure, as defined by the appended claims, and may alternatives, modifications, and variations will be apparent to those skilled in the art.

What is claimed is:

1. An apparatus for measuring bio-information, the apparatus comprising:
   a light source comprising a green light emitter configured to emit green light of a green wavelength range, and an infrared light emitter configured to emit infrared light of a infrared wavelength range;

an image sensor comprising an n number of pixel rows, n denotes a number that is equal to or greater than 10, wherein:

among the n number of pixel rows, a first set of alternating number rows comprises a plurality of green pixels configured to detect the green light and reacted with an object, without detecting the infrared light, and among the n number of pixel rows, a second set of alternating number rows comprises a plurality of infrared pixels configured to detect the infrared light and reacted with the object, without detecting the green light, wherein the second set of alternating number rows alternates with the first set of alternating number rows; and a pixel controller configured to control the image sensor row-by-row to simultaneously activate the plurality of green pixels in a first pixel row while simultaneously deactivating the plurality of infrared pixels in a second pixel row during a first time period, and simultaneously activate the plurality of infrared pixels in the second pixel row while simultaneously deactivating the plurality of green pixels in the first pixel row during a second time period;

a light source controller configured to control the green light emitter to emit the green light when a green light exposure operation is performed on the plurality of green pixels, and control the infrared light emitter to emit the infrared light when a infrared light exposure operation is performed on the plurality of infrared pixels; and a processor configured to:

for one frame of the image sensor, obtain a green photoplethysmogram (PPG) signal based on green light signals detected by the first set of alternating number rows of the image sensor, and obtain an infrared PPG signal based on infrared light signals detected by the second set of alternating number rows of the image sensor; and estimate blood pressure of the object based on the green PPG signal and the infrared PPG signal, wherein the light source is provided separately from the image sensor, wherein the image sensor is further configured to output a horizontal synchronization (H-sync) signal that alternates between a high state and a low state upon a completion of a read-out operation of each pixel row, and wherein, based on the H-sync signal provided from the light source to the light source controller, the light source controller is further configured to alternate on and off states of the green light emitter and the infrared light emitter every occurrence of a predetermined number of consecutive high states of the H-sync signal.

2. The apparatus of claim 1, wherein the pixel controller is further configured to generate pixel control signals and timing signals for controlling the plurality of green pixels and the plurality of infrared pixels, and wherein the light source controller is further configured to control the light source based on the pixel control signals or the timing signals.

3. The apparatus of claim 2, wherein the pixel control signals comprise a reset signal, and the timing signals comprise the H-synch signal, and wherein the light source controller is further configured to control the light source based on the reset signal or the H-sync.

4. The apparatus of claim 1, wherein the light source controller is further configured to:

during the first time period, activate all the plurality of green pixels in the first pixel row and perform a first electronic shutter operation and the green light exposure operation in sequence, and deactivate all the plurality of infrared pixels in the second pixel row, during the second time period, activate all the plurality of infrared pixels in the second pixel row and perform a second electronic shutter operation and the infrared light exposure operation in sequence, and deactivate all the plurality of green pixels in the first pixel row, and during an intermediate period between the first time period and the second time period, deactivate all the plurality of green pixels and all the plurality of infrared pixels and perform the read-out operation on the plurality of green pixels.

5. The apparatus of claim 1, wherein the light source further comprises another light emitter configured to emit light of a wavelength range different from the green light and the infrared light.

6. The apparatus of claim 1, further comprising a force sensor disposed on the image sensor to measure a force exerted onto the apparatus.

7. An electronic device comprising:

the apparatus of claim 1; and a speaker or a display device configured to output information measured by the apparatus.

8. A method of measuring bio-information, the method comprising:

based on a pixel control signal or a timing signal which is generated by an image sensor, driving a first light emitter to emit first light of a first wavelength range, wherein the image sensor comprises an n number of pixel rows, n denotes a number that is equal to or greater than 10;

detecting the first light of the first wavelength range, which is reacted with an object, by using, among the n number of pixel rows, a first set of alternating number rows comprising a plurality of first pixels of the image sensor and that are not configured to detect second light of a second wavelength range;

based on the pixel control signal or the timing signal which is generated by the image sensor, driving a second light emitter to emit the second light of the second wavelength range;

detecting the second light of the second wavelength range, which is reacted with the object, by using, among the n number of pixel rows, a second set of alternating number rows comprising a plurality of second pixels of the image sensor, wherein the second set of alternating number rows alternates with the first set of alternating number rows;

controlling the image sensor row-by-row to simultaneously activate the plurality of first pixels while simultaneously deactivating the plurality of second pixels during a first time period, and to simultaneously activate the plurality of second pixels while simultaneously deactivating the plurality of first pixels during a second time period; and estimating blood pressure of the object based on a first photoplethysmogram (PPG) signal and a second PPG signal that are obtained from the first light signals detected by the first set of alternating number rows of the image sensor and the second light signals detected by the second set of alternating number rows of the image sensor, respectively, for one frame of the image sensor, wherein the first light emitter and the second light emitter are provided separately from the image sensor, wherein the method further comprises outputting a horizontal synchronization (H-sync) signal that alternates between a high state and a low state upon a completion of a read-out operation of each pixel row, and based on the H-sync signal provided from a light source including the first light emitter and the second light emitter to a light source controller, alternating on and off states of the first light emitter and the second light emitter, by the light source controller, every occurrence of a predetermined number of consecutive high states of the H-sync signal.

9. The method of claim 8, wherein the first time period during which a first light exposure operation is performed on the first set of alternating number rows does not overlap the second time period during which a second light exposure operation is performed on the second set of alternating number rows.

10. The method of claim 8, further comprising measuring a force exerted by the object onto an apparatus comprising the first emitter, the second emitter, and the image sensor.

11. The method of claim 8, wherein the pixel control signal is a pixel reset signal, and wherein the driving the first light emitter and the driving the second light emitter comprise driving the first light emitter based on the pixel reset signal, and driving the second light emitter based on the pixel reset signal, respectively.

12. An apparatus for measuring bio-information, the apparatus comprising:

a light source configured to emit first light of a first wavelength range and second light of a second wavelength range to an object;

an image sensor comprising an n number of pixel rows, n denotes a number that is equal to or greater than 10, wherein:

among the n number of pixel rows, a first set of alternating number rows comprises a plurality of first pixels which are exposed to the first light together at a first time period;

among the n number of pixel rows, a second set of alternating number rows comprises a plurality of second pixels which are exposed to the second light together at a second time period, wherein the second set of alternating number rows alternates with the first set of alternating number rows; and a pixel controller configured to control the image sensor line-by-line to simultaneously activate the plurality of first pixels while simultaneously deactivating the plurality of second pixels during the first time period, and simultaneously activate the plurality of second pixels while simultaneously deactivating the plurality of first pixels during the second time period, a light source controller configured to control the light source to emit the first light during the first time period, and control the light source to emit the second light during the second time period; and a processor configured to:

for one frame of the image sensor, obtain a first photoplethysmogram (PPG) signal based on first light signals detected by the first set of alternating number rows of the image sensor, and obtain an second PPG signal based on second light signals detected by the second set of alternating number rows of the image sensor, and estimate blood pressure of the object based on the first PPG signal and the second PPG signal, wherein the light source is provided separately from the image sensor, wherein the image sensor is further configured to output a horizontal synchronization (H-sync) signal that alternates between a high state and a low state upon a completion of a read-out operation of each pixel line, and wherein, based on the H-sync signal provided from the light source to the light source controller, the light source controller is further configured to alternate on and off states of the first time period for emitting the first light and the second time period for emitting the second light every occurrence of a predetermined number of consecutive high states of the H-sync signal.

* * * * *